US008078255B2

(12) United States Patent
Bhandarkar et al.

(10) Patent No.: US 8,078,255 B2
(45) Date of Patent: Dec. 13, 2011

(54) VIRTUAL SURGICAL SYSTEMS AND METHODS

(75) Inventors: Suchendra M. Bhandarkar, Watkinsville, GA (US); Ernest William Tollner, Bogart, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 1232 days.

(21) Appl. No.: 11/693,535

(22) Filed: Mar. 29, 2007

(65) Prior Publication Data

US 2008/0004517 A1 Jan. 3, 2008

Related U.S. Application Data

(60) Provisional application No. 60/786,980, filed on Mar. 29, 2006.

(51) Int. Cl.
*A61B 5/05* (2006.01)
*G06K 9/00* (2006.01)

(52) U.S. Cl. ........ 600/407; 382/128; 382/129; 382/130; 382/131; 382/132

(58) Field of Classification Search .......... 382/128–132; 600/407
See application file for complete search history.

(56) References Cited

U.S. PATENT DOCUMENTS 5,682,886 A * 11/1997 Delp et al. ............... 600/407
6,701,174 B1 * 3/2004 Krause et al. ............ 600/407

OTHER PUBLICATIONS

Chowdhury et al. ("A Novel Multifaceted Virtual Craniofacial Surgery Scheme using Computer Vision", Y. Liu, T. Jiang, and C. Zhang (Eds.): CVIBA 2005, LNCS 3765, pp. 146-159, Oct. 2005).*
A.S. Chowdhury, S.M. Bhandarkar, E.W. Tollner, G. Zhang, J.C. Yu, and E. Ritter, A Novel Multifaceted Virtual Craniofacial Surgery Scheme Using Computer Vision, Proc. IEEE Workshop on Computer Vision for Biomedical Image Applications: Current Techniques and Future Trends (CVBIA 2005), at the Int'l. Conf. Computer Vision, Beijing, China, Oct. 2005, Y Liu, T. Jiang and C. Zhang (Eds.), Springer LNCS vol. 3765, pp. 146-159.
A.S. Chowdhury, S.M. Bhandarkar, G. Datta, and J.C. Yu, Automated Detection of Stable Fracture Points in Computed Tomography Image Sequences, Proc. IEEE Intl. Symposium on Biomedical Imaging (ISBI 2006), Arlington, VA, Apr. 2006, pp. 1320-1323.
A.S. Chowdhury, A. Bhattacharya, S.M. Bhandarkar, G.S. Datta, J.C. Yu, and R. Figueroa, Hairline Fracture Detection Using MRF and Gibbs Sampling, Proc. IEEE Workshop on Applications in Computer Vision (WACV 2007), Austin, TX, Feb. 21-22, 2007, in press.
A.S. Chowdhury, S.M. Bhandarkar, R.W. Robinson, and J.C. Yu, Virtual Craniofacial Reconstruction from Computed Tomography Image Sequences Exhibiting Multiple Fractures, Proc. IEEE Intl. Conf. Image Processing (ICIP 2006), Atlanta, GA, Oct. 2006, pp. 1173-1176.

* cited by examiner

*Primary Examiner* — Anand Bhatnagar
*Assistant Examiner* — Amara Abdi
(74) *Attorney, Agent, or Firm* — Thomas, Kayden, Horsteymeyer & Risley, LLP

(57) ABSTRACT

Various embodiments of virtual surgical systems and methods are disclosed.

3 Claims, 12 Drawing Sheets

VIRTUAL SURGICAL SYSTEMS AND METHODS

CROSS-REFERENCE TO RELATED APPLICATIONS

This application claims priority to, and the benefit of, U.S. Provisional Patent Application entitled "Virtual Surgical Systems and Methods," assigned Ser. No. 60/786,980, and filed on Mar. 29, 2006, which is incorporated by reference in its entirety.

This application is related to pending PCT Patent Application entitled "Virtual Surgical Systems and Methods," assigned Serial No. PCT US 05/12504, and filed on Apr. 13, 2005, which claims the benefit of U.S. Provisional Patent Application entitled "Virtual Surgical Systems and Methods," assigned Ser. No. 60/561,584, and filed on Apr. 13, 2004, each of which is incorporated by reference in its entirety.

TECHNICAL FIELD

The present disclosure is generally related to computer systems and, more particularly, is related to computer systems for virtual surgery implementations.

BACKGROUND

Traumatic impact of the skeleton may require extensive surgery to re-align fragmented skeletal features. Although any alignment of bone fragments requires a degree of precision, restoring the form and function of the bone fragments in the craniofacial skeleton is particularly challenging because of the strict tolerances required.

During conventional craniofacial surgery, a plastic surgeon restores the form and function of the bone fragments in the craniofacial skeleton by first exposing all the fragments (e.g., by removing any fleshy tissue surrounding the fragments). This visualization is necessary to determine how the bone fragments should fit together for a reduction of the fracture(s). Next, the fracture(s) are reduced by bringing the displaced or broken bones to a desired configuration position (e.g., returned back to their pre-fractured positions). The reduction is typically performed by manually manipulating the bone fragments to the desired configuration. Once the fracture(s) are reduced, the aligned bone fragments are maintained in this configuration with a prosthesis.

The prosthesis may comprise of, for example, rigid screws and plates and/or bone grafts, which are used to maintain the aligned bone fragments together. The screws, plates, and/or grafts may be made of metals or synthetic materials, such as plastics. Typically, the decision as to the type and configuration (e.g., dimensions, form, rigidity, etc.) of the prosthesis is made during the surgical procedure such that the surgeon has a visual depiction of the contours of the fragments once aligned. The surgeon can then use this visual depiction to determine the type and configuration of the prosthesis. A machine room may be located in close proximity to the operating room to fabricate the necessary prosthesis during the operation.

There are several problems with this current, standard approach. To visualize the fragments (e.g., in order to align them and to determine the prosthesis to use) necessitates their exposure, which reduces the blood supply to the bodily area of the fracture. To improve the blood supply, the surgeon can decrease the extent of dissection. However, with decreased dissection, the surgeon is not able to visualize the entire fracture, which could lead to potential mal-alignments of the bone fragments. Further, because the surgeon does not determine the type and configuration of the prosthesis to use until the surgery is underway, the surgery is prolonged while the prostheses is configured or manufactured appropriately. This results in extended periods of time in which the patient remains anesthetized and dissected, increasing the chance of surgical complications and tying up valuable surgical resources such as surgical clean rooms, surgeons, nurses, and anesthesiologists, etc.

BRIEF DESCRIPTION OF THE DRAWINGS

Many aspects of a computer-aided, virtual (i.e., in silico) surgical system and the underlying methods can be better understood with reference to the following drawings. The components in the drawings are not necessarily to scale, emphasis instead being placed upon clearly illustrating the principles of a virtual surgical system and the underlying methods. Moreover, in the drawings, like reference numerals designate corresponding parts throughout the several views.

SUMMARY

Figure 1:
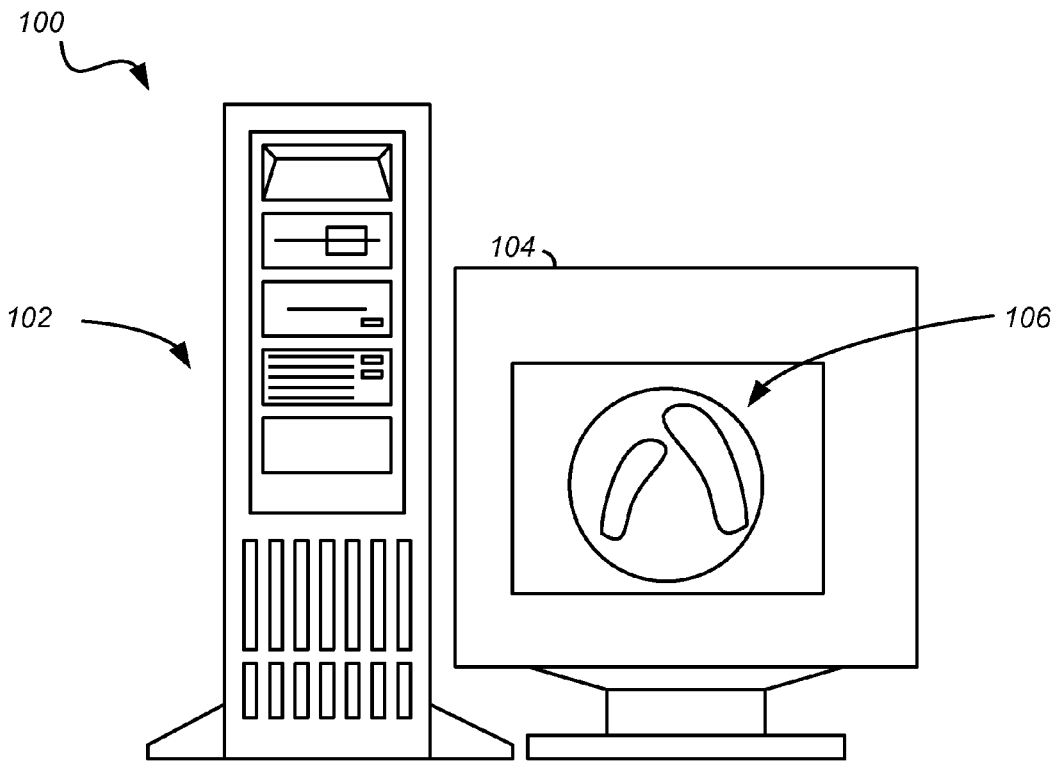
FIG. 1 is an embodiment of a computer system that may be used to implement an embodiment of a virtual surgical system.

Systems and methods for providing virtual alignment of fractured surfaces are provided.

One method embodiment, among others, comprises receiving image slices corresponding to an imaged object having a hairline fracture, the image slices each comprising a plurality of pixel blocks; fitting quadratic polynomial functions to inner and outer contours of the imaged object for select pixel blocks less than the entire plurality of the pixel blocks for each of the images slices; and iteratively sampling the select pixel blocks based on Markov random field modeling and maximum a posteriori estimation to visualize the hairline fracture.

Another method embodiment, among others, comprises matching fragment surfaces of an imaged object with a data aligned rigidity constrained exhaustive search (DARCES) surface matching algorithm that uses fragment surface data sets to produce a transformed sample data set for at least one of the fragment surfaces; matching the fragment surfaces with an iterative closest point (ICP) algorithm that uses the transformed sample data set; and minimizing a mean-squared error between the matched fragment surfaces based on iterative angular perturbations until a desired reconstruction is achieved.

Another method embodiment, among others, comprises receiving data corresponding to image slices of an imaged object comprising a fracture; determining potential fracture points of the imaged object from the data based on a curvature scale space algorithm; filtering out one or more of the potential fracture points; and determining which of the remaining fracture points are stable across a predetermined number of the image slices based on a Kalman filter that provides surface data for the fracture.

Another method embodiment, among others, comprises identifying at least two fracture surface pairs based on a maximum weight graph matching algorithm; modeling the fracture surfaces as vertices of a general graph; compiling a score matrix comprising edge weights between the vertices of the fracture surface pairs to determine opposing fracture surface pairs; and registering the opposing fracture surface pairs.

One system embodiment, among others, comprises a memory with software stored therein, and a processor configured with the software to match fragment surfaces of an imaged object with a data aligned rigidity constrained exhaustive search (DARCES) surface matching algorithm that uses fragment surface data sets to produce a transformed sample data set for at least one of the fragment surfaces, match the fragment surfaces with an iterative closest point (ICP) algorithm that uses the transformed sample data set, and minimize a mean-squared error between the matched fragment surfaces based on iterative angular perturbations until a desired reconstruction is achieved.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

DETAILED DESCRIPTION

Embodiments of virtual surgical systems, and the underlying methods, are disclosed (herein referred to as a virtual surgical system for brevity). The virtual surgical systems may be used for providing pre-operative, virtual depiction of fragmented, or fractured objects (e.g., bone fragments, hairline fractures, etc.).

As defined medically, the reduction of fractured surfaces includes the restoration of an injured or dislocated object to its pre-fractured anatomical relation. For example, if an object such as a bone is fractured, the resulting surfaces of the fractured bone are oriented such that the fractured pieces are restored to their pre-fractured position with respect to each other. In a non-virtual environment, this reduction typically includes physically manipulating the fragmented bone surfaces to restore the bone fragments to their pre-fractured position.

In a virtual environment, such as the disclosed virtual surgical system, reduction relates to simulating the manipulation of the fragmented objects to provide a reconstructed object in which the fragments are restored to their pre-fractured position. Thus, the resulting "virtual" reduction may provide an image representing the restored object.

In general, one embodiment of a virtual surgical system receives an image, such as a computer tomography (CT) scan, of an area of the patient in need of surgical reconstruction (e.g., in the event of a bone fracture) prior to an incision being made in a surgery. Fragments that are to be reduced are selected using the virtual surgical system. The system performs surface matching techniques using surface data representing the contour of the end surfaces of the fragments to determine how the corresponding fragments should be oriented to perform the reduction. At least one of the fragments may then be transformed (e.g., via translation and/or rotation) to join the surfaces based on the matched surfaces. An image may then be generated of the reconstructed area. Accordingly, the generation of the image of the reconstructed area may occur before an incision is made. Thus, before actual dissection of the area, and the subsequent surgical reduction of the bones, an image of the reconstructed area may be displayed such that a proper prosthesis may be determined and/or manufactured.

Such a system has a number of potential advantages over current surgical procedures that do not provide the capability to preview an image of the reconstructed object. For example, the virtual surgical system minimizes risks to the patient by potentially reducing the amount of dissection required during surgery. Furthermore, the time required for the surgical procedure is potentially reduced by providing the ability to pre-select and/or manufacture an appropriate prosthesis for securing the fragmented objects once reduced.

Thus, one embodiment of a virtual surgical system includes enabling technology that may incorporate computer vision, computer visualization, and computer-aided design and manufacturing (CAD/CAM) to reconstruct the craniofacial skeleton and reduce the fractures "in silico" (i.e., within a virtual environment created using the computer). Although embodiments are described in the context of performing surgery on a craniofacial skeleton, the virtual surgical system embodiments are not limited to craniofacial applications. Rather, the virtual surgical system may be used for many types of reconstructive surgery, including orthopedic surgery, and in general, the reconstruction of objects having fractures.

Various embodiments of virtual surgical systems and methods are described in PCT Patent Application Serial No. PCT US 05/12504, entitled "Virtual Surgical Systems and Methods" (the '504 application) and referenced above. The present disclosure includes additional systems and method embodiments which build upon embodiments of the systems and methods of the '504 application.

According to one embodiment, the surface matching algorithms used to align the fractured surfaces described in the '504 application can be enhanced with the incorporation of a biomechanical stability term and a global shape-based symmetry term in the surface matching objective function. Accordingly, instead of performing surface matching in a single phase using the Data Aligned Rigidity Constrained Exhaustive Search (DARCES), the Iterative Closest Point (ICP) algorithm or the DARCES-ICP hybrid algorithm as described in the '504 application (e.g., see FIG. 8 and related text), two phases are employed.

In the first phase, the DARCES-ICP hybrid algorithm is used to align the fracture surfaces using minimum mean squared error as the matching metric. In the second phase, a local angular perturbation scheme is used to optimize an objective function that incorporates global shape symmetry and biomechanical stability. Such an embodiment can be used to result in a more accurate reconstruction.

According to another embodiment, the process of manually delineating the points along the fracture contours in individual CT image slices, as described in the '504 application, can be replaced by an automatic fracture point detection scheme. That is, in the previously described embodiments, the fracture contours are manually delineated in individual CT image slices and these fracture contours from individual image CT slices are then collated to generate the fracture surfaces. In contrast, according to one embodiment of the present disclosure, a scheme is presented for automatically detecting the fracture contours in individual CT image slices and generating the fracture surfaces therefrom.

For example, the fracture contours can be detected by first identifying fracture points or corner points in the CT image slices using techniques based on curvature scale space theory and graph based filtering. Once the fracture points or corner points have been identified, a novel Kalman filter is then used to determine fracture corners that are stable across a sufficient number of CT image slices. Fracture contours can then be identified using the stable fracture corners as bounds and are then collated to automatically generate the fracture surface data.

According to another embodiment, the ability to align and depict fragmented objects having multiple fractures is provided. That is, previously described embodiments of the virtual surgical systems (in the '504 application) were designed primarily for single fracture scenarios. However, according to embodiments described herein, the capabilities of the virtual surgical systems and methods are enhanced to deal with multiple fractures.

For example, according to some embodiments, the opposable fracture surfaces are determined using a maximum weight graph matching algorithm. Once the opposable fracture surfaces are determined, the surfaces are placed in coarse alignment. The fracture surfaces can then be modeled as vertices of a general graph, and the edge weights can be computed using a combination of the Hausdorff distance and a score function based on the fracture surface characteristics. The coarse alignment of the fracture surfaces is subsequently refined using any of the surface matching algorithms designed for single fracture scenarios. Such algorithms may include, for example, those described in the '504 application and/or herein.

According to another embodiment, hairline fractures are addressed. The frequently encountered craniofacial and mandibular fractures described in the '504 application are often observed to possess distinct patterns in X-ray or CT images. In some cases, the fractures are observed to be hairline or minor in nature. The term hairline fracture or minor fracture generally refers to those situations where the broken bone fragments are not visibly out of alignment. In the presence of noise, for instance, the detection and subsequent visualization of hairline fractures is a clinically challenging task. In the present disclosure, certain embodiments provide for hairline fracture detection (e.g., mandibular fracture detection) in CT images based on Markov Random Field (MRF) modeling and Gibbs sampling. Such hairline fracture detection approaches are additionally capable of target pattern generation (e.g., provides a method to predict how a jaw with a hairline fracture would appear if allowed to heal naturally without explicit surgical intervention). Such target pattern generation may have potential prognostic significance because surgeons can use this to help decide if open surgical reduction and fixation is indicated or if the fractures can be managed by allowing them to heal spontaneously based on what the spontaneously healed mandible will be or look like.

Accordingly, now that a brief summary of the various embodiments of the virtual surgical systems and methods have been described, each of these approaches are now described in more detail below.

FIG. 1 is a schematic diagram that depicts a computer 100 in which embodiments of a virtual surgical system 102 may be implemented. The computer 100 can be a general purpose or special digital computer, such as a personal computer (PC; IBM-compatible, Apple-compatible, or otherwise), workstation, minicomputer, or mainframe computer. The computer 100 may be in a stand-alone configuration or may be networked with other computers. The computer may form part of a CT scanner, x-ray imaging machine, magnetic resonance imaging (MRI) device, sonogram device, a robotic/telerobotic surgical system, or telerobotic surgical interface. The computer 100 includes a display terminal 104 that can provide a graphical model 106 of a CT image. The CT image may depict a portion of the skeletal structure having suffered a fracture, such as the fractured mandible depicted in the graphical model 106 of FIG. 1. Although the graphical model 106 depicts the mandible along one axis, the graphical model 106 can be displayed in a variety of perspectives.

The virtual surgical system 102 can be implemented in software, firmware, hardware, or a combination thereof. In one embodiment, the virtual surgical system 102 is implemented in software, as an executable program that is executed by the computer 100.

Figure 2:
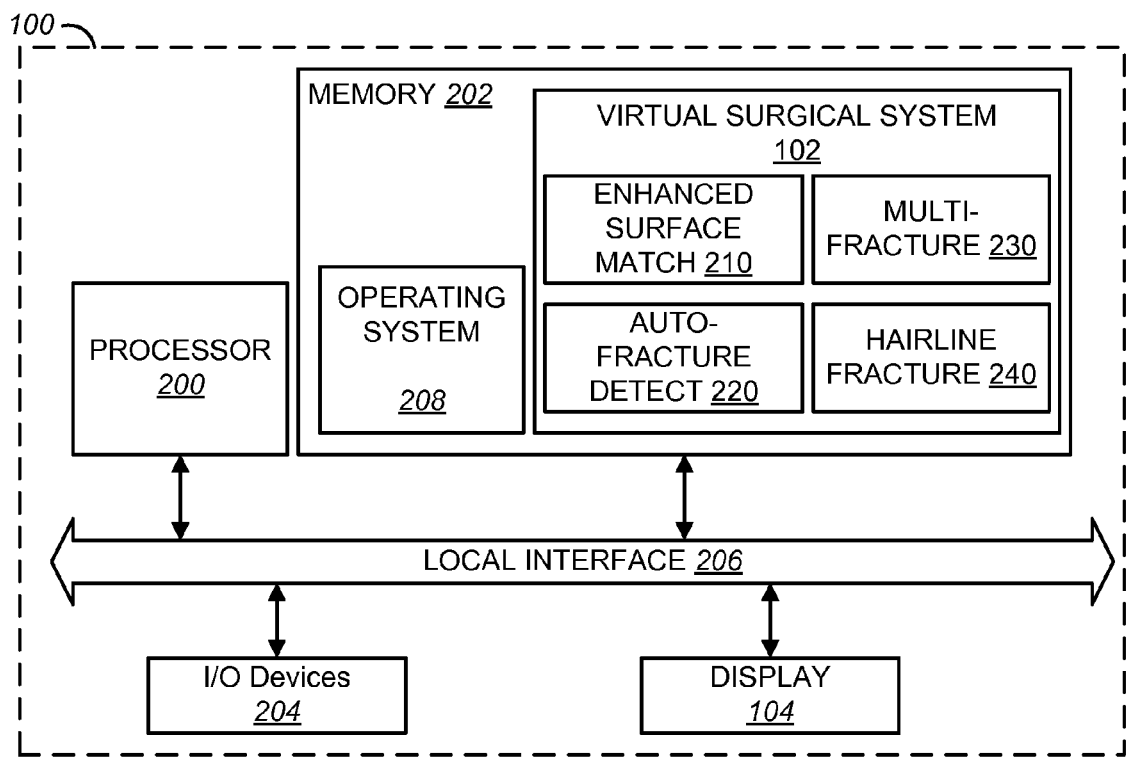
FIG. 2 is a block diagram that illustrates an embodiment of a configuration of the computer shown in FIG. 1 for implementing an embodiment of a virtual surgical system.

FIG. 2 is a block diagram showing an embodiment of a configuration of the computer 100 implementing virtual surgical system 102. Generally, in terms of hardware architecture, the computer 100 includes a processor 200, a memory 202, display 104, and one or more input and/or output (I/O) devices 204 (or peripherals) that are communicatively coupled via a local interface 206. The local interface 206 may be, for example, one or more buses or other wired or wireless connections. The local interface 206 may have additional elements such as controllers, buffers (caches), drivers, repeaters, and receivers, to enable communication. Further, the local interface 206 may include address, control, and/or data connections that enable appropriate communication among the aforementioned components. It should be understood that the computer 100 may comprise a number of other elements, such as, but not limited to, storage devices, optical drives, and networking hardware, which have been omitted for the purposes of brevity.

The processor 200 is a hardware device for executing software, particularly that which is stored in memory 202. The processor 200 may be any custom made or commercially available processor, a central processing unit (CPU), an auxiliary processor among several processors associated with the computer 100, a semiconductor-based microprocessor (in the form of a microchip or chip set), a macroprocessor, or generally any device for executing software instructions.

The memory 202 may include any one, or a combination of, volatile memory elements (e.g., random access memory (RAM)) and nonvolatile memory elements (e.g., ROM, hard drive, etc.). Moreover, the memory 202 may incorporate electronic, magnetic, optical, and/or other types of storage media. Note that the memory 202 may have a distributed architecture in which the various components are situated at locations that are remote from one another but may be accessed by the processor 200.

In addition to the memory 202 being used for the storage of data (such as the data corresponding to graphical model 106), the memory 202 may include one or more separate executable programs, each of which comprises an ordered listing of executable instructions for implementing logical and arithmetic functions (i.e. software). In the example of FIG. 2, the software in the memory 202 may include an embodiment of the virtual surgical system 102 and a suitable operating system 208. The operating system 208 essentially controls the execution of other computer programs, such as the virtual surgical system 102, and provides scheduling, input-output control, file and data management, memory management, and communication control and related services.

Certain embodiments of the virtual surgical system 102 comprise one or more of the following modules that enhance the functionality of the virtual surgical system 102: en enhanced surface matching module 210, an auto-fracture detection module 220, a multi-fracture detection module 230, and a hairline fracture detection module 240. Each of these modules, and in particular, the processes they implement, is described below.

The virtual surgical system 102 (including the modules of the same) may be a source program, executable program (object code), script, or any other entity comprising a set of instructions to be performed. As is described below, the virtual surgical system 102 can be implemented, in one embodiment, as a distributed network of modules, where one or more of the modules can be accessed by one or more applications or programs or components thereof. In other embodiments, the virtual surgical system 102 can be implemented as a single module with all of the functionality of the aforementioned modules. The source program may be loaded in the memory 202 so as to be capable of being executed to operate properly in connection with the operating system 208. Furthermore, the virtual surgical system 102 can be written with (a) an object oriented programming language, which has classes of data and methods, or (b) a procedural programming language, which has routines, subroutines, and/or functions, for example but not limited to, C, C++, Pascal, Basic, Fortran, Cobol, Perl, Java, and Ada.

The I/O devices 204 may include input devices such as, for example, a keyboard, mouse, scanner, microphone, etc. Furthermore, the I/O devices 204 may also include output devices such as, for example, a printer, etc. The I/O devices 204 may further include devices that communicate both inputs and outputs such as, for instance, a modulator/demodulator (modem for accessing another device, system, or network), a radio frequency (RF) or other transceiver, a telephonic interface, a bridge, a router, etc. The I/O devices 204 may also include imaging devices, which may include medical imaging devices, such as, CT imaging devices, X-ray machines, magnetic resonance imaging (MRI) devices, sonogram devices, a robotic/telerobotic surgical system, or telerobotic surgical interface.

When the computer 100 is in operation, the processor 200 is configured to execute software stored within the memory 202, to communicate data to and from the memory 202, and to generally control operations of the computer 100 pursuant to the software. The virtual surgical system 102 and the operating system 208, in whole or in part, but typically the latter, are read by the processor 200, perhaps buffered within the processor 200, and then executed.

When the virtual surgical system 102 is implemented in software, as is shown in FIG. 2, it should be noted that the virtual surgical system 102 can be stored on any computer-readable medium for use by, or in connection with, any computer-related system or method. In the context of this document, a computer-readable medium is an electronic, magnetic, optical, or other physical device or means that can contain or store a computer program for use by, or in connection with, a computer related system or method. The virtual surgical system 102 can be embodied in any computer-readable medium for use by or in connection with an instruction execution system, apparatus, or device, such as a computer-based system, processor-containing system, or other system that can fetch the instructions from the instruction execution system, apparatus, or device and execute the instructions.

In an alternative embodiment, where the virtual surgical system 102 is implemented in hardware, the virtual surgical system 102 can be implemented with any or a combination of the following technologies, which are each well known in the art: (a) discrete logic circuit(s) having logic gates for implementing logic functions upon data signals, an application-specific integrated circuit (ASIC) having appropriate combinational logic gates, (a) programmable gate array(s) (PGA), a field programmable gate array (FPGA), etc; or can be implemented with other technologies now known or later developed.

Figure 3:
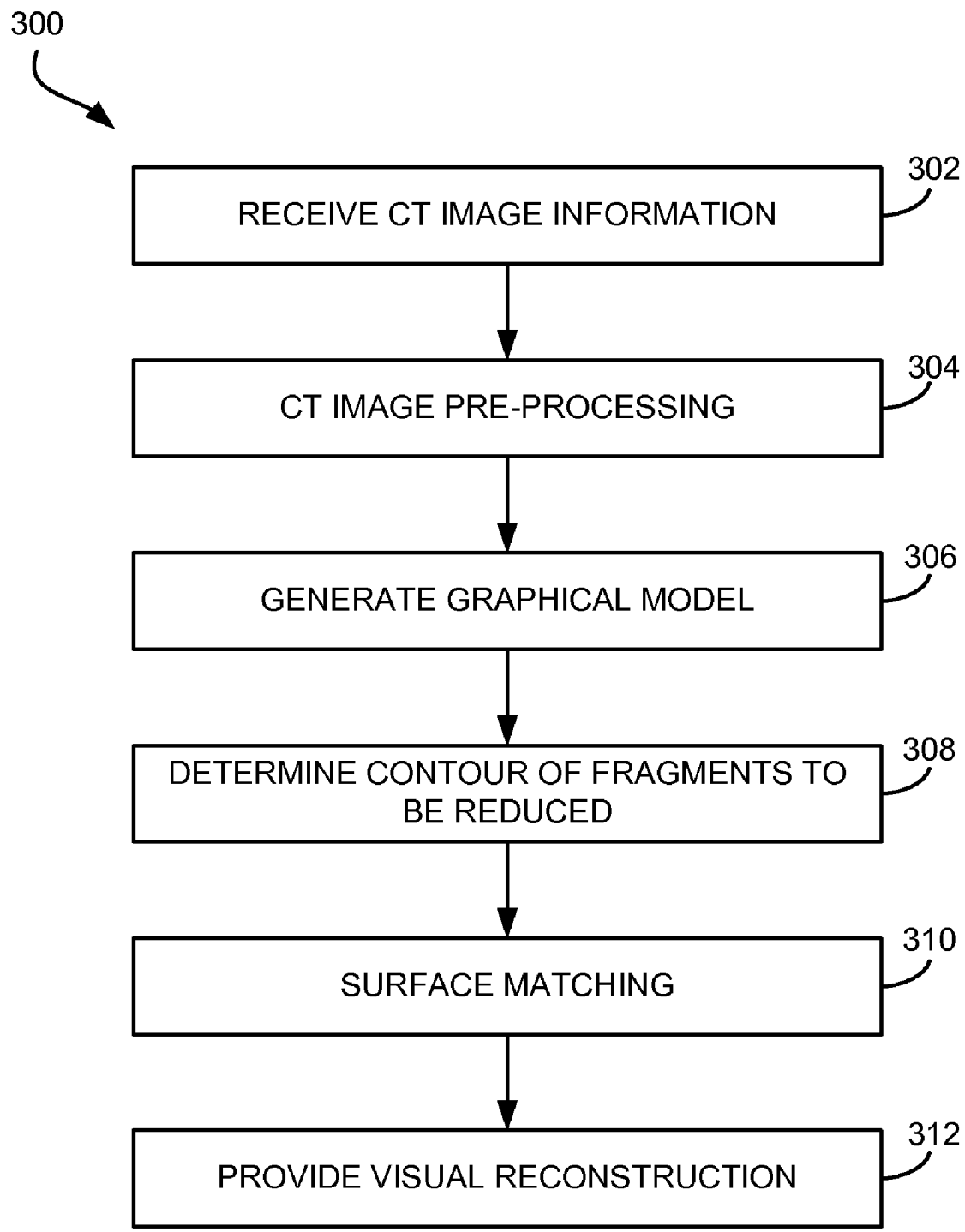
FIG. 3 depicts a flow diagram that illustrates one embodiment of a method employed by the virtual surgical system shown in FIGS. 1 and 2.

FIG. 3 is a flow diagram that illustrates one embodiment of a method employed by the virtual surgical system 102. Any process descriptions, steps, or blocks in flow diagrams described herein should be understood as potentially representing modules, segments, or portions of code which include one or more executable instructions for implementing specific logical functions or steps in the process, and alternate implementations are included within the scope of the preferred embodiments of the virtual surgical system 102 in which functions may be executed out of order from that shown or discussed, including substantially concurrently or in reverse order, depending on the functionality involved, as would be understood by those reasonably skilled in the art.

As depicted in the method embodiment 300, step 302 includes receiving information representing at least one digital image of fragmented bone elements. For example, one input of digital image information to the virtual surgical system 102 may be a sequence of grayscale images of a fractured human mandible. In the present embodiment, the images are two-dimensional (2-D) computer tomography (CT) image slices. In one embodiment, exemplary dimensions and color features for the CT image slices may be 150 millimeter (mm)×150 mm with an 8-bit color depth. The digital image information may be provided, for example, across local interface 206 from input devices 204.

Figure 4:
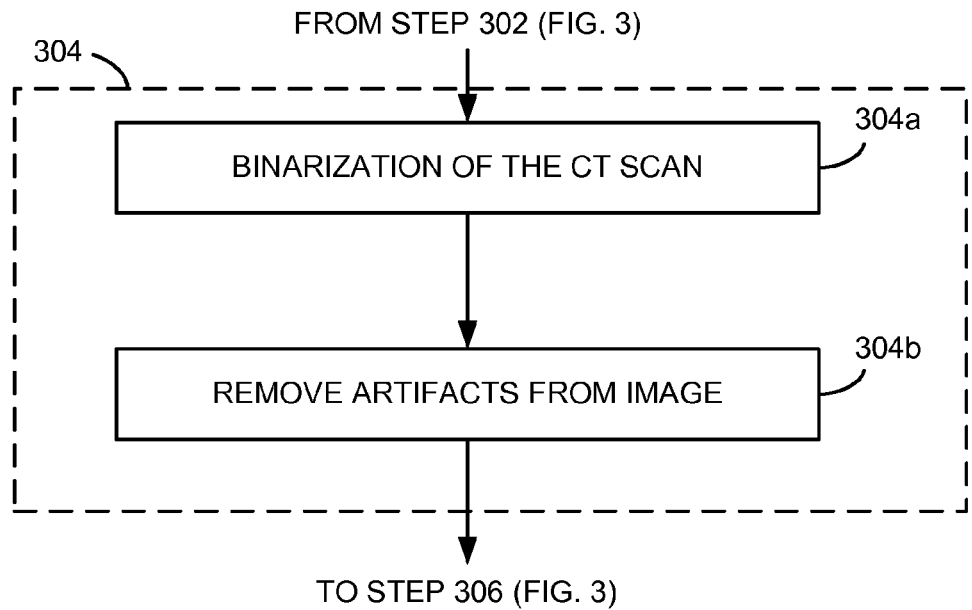
FIG. 4 depicts a flow diagram that illustrates one embodiment of an image pre-processing method that may be used with the method of FIG. 3.

Step 304 includes pre-processing the digital image information (e.g., the CT image). Specifically, as depicted in FIG. 4, in one embodiment, a series of image pre-processing tasks 304a-304b are undertaken by the virtual surgical system 102 before using the surface matching algorithms to obtain the desired goal of reduction (i.e., alignment) of the fracture surfaces. It should be understood that, rather than performing some, or all, of the preprocessing tasks, in some embodiments, pre-processed images may be presented as input to the virtual surgical system 102 at step 302.

One pre-processing task that may be performed by the virtual surgical system 102 includes thresholding for binarization of the digital image. That is, a digital image representing objects such as bone fragments may be simplified by determining the objects of interest in the image, and representing those objects with one or more pixel values associated with the object of interest. The objects of interest may be, for example, bone fragments to be joined, but may also include other artifacts, such as objects having densities similar to bone (e.g., other bones, medical instruments, etc.).

Thus, at step 304, according to the present embodiment, the virtual surgical system 102 may classify a pixel with a particular value as belonging to the object of interest. For example, grayscale images assign the number 0 to pure black and the number 255 to pure white. The scale assigns varying shades of gray from dark to light to the whole numbers in between. Thus, in the current embodiment, a grayscale from 0 to 255 levels may represent 256 colors. Accordingly, the virtual surgical system 102 may classify each pixel in a received image with a gray scale value above (or below, in the case of a negative image) a particular level (e.g., 250) to belong to the objects of interest. Any pixel having a value above the threshold level may then be represented using a single color. The threshold value may be selected iteratively by trial and error to arrive at the best representation of the object of interest.

Figure 9:
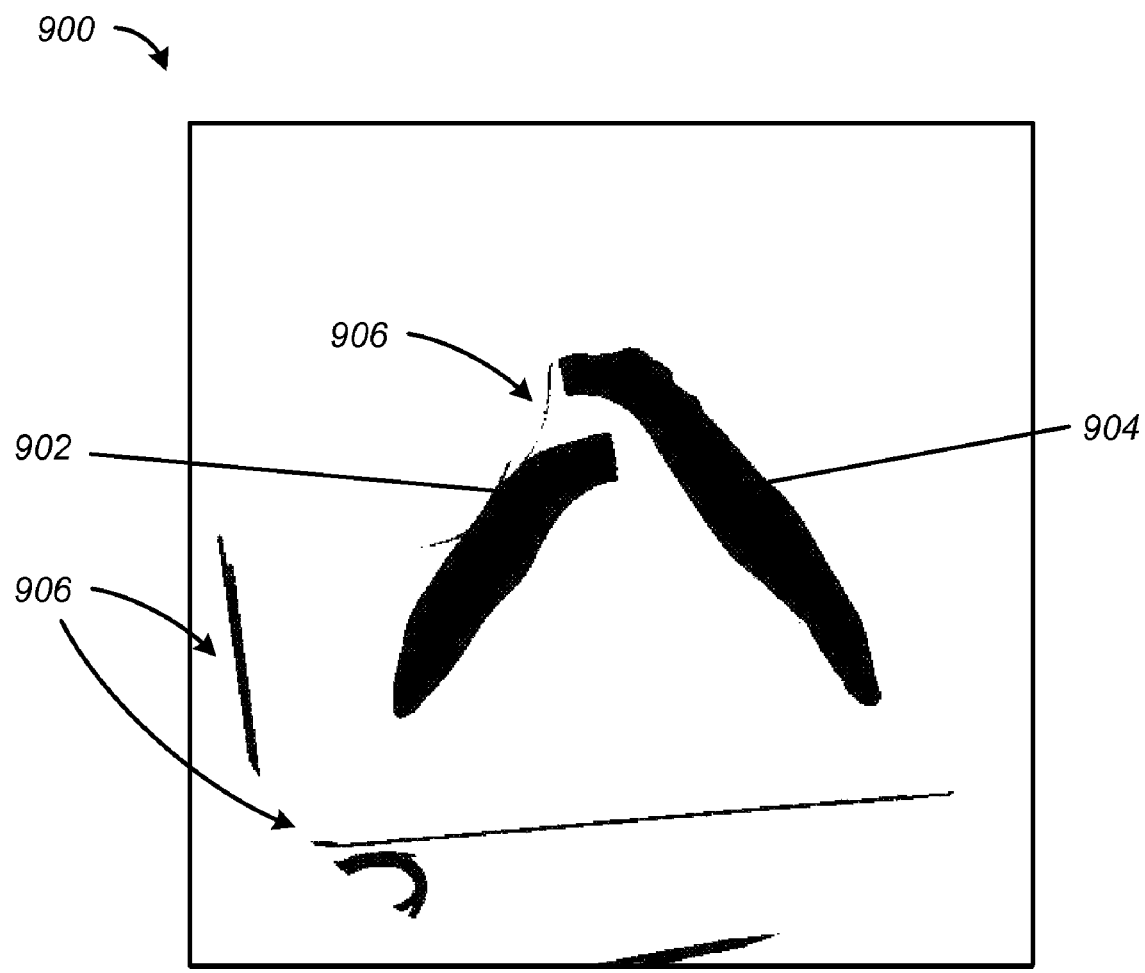
FIG. 9 is a picture of a Computer Tomography (CT) image slice depicting two broken fragments of a human mandible as a result of a thresholding operation performed by the method of FIG. 4.

As an example, a raw CT image slice comprising a number of pixels having grayscale values may undergo the thresholding of step 304, resulting in the binary CT image slice 900 of FIG. 9. Each pixel in the raw CT image slice can be analyzed against a predetermined threshold value of 250. The resulting binary image slice depicts the objects of interest as represented by the single color of black (e.g., a pixel value of 0), and pixels not meeting the threshold are represented by a single color of white (e.g., a pixel value of 1). The resulting binary image B(i, j) for the gray scale CT image slice G(i, j) is given by:

$$B(i, j) = \begin{cases} 0 & \text{if } (G(i, j) > 250 \\ 1 & \text{otherwise} \end{cases} \quad \text{(Eq. 1)}$$

Binarization by itself may not distinctly represent the two fractured fragments 902 and 904, as can be seen from FIG. 9. For example, in some embodiments, undesired artifacts 906, unrelated to the objects of interest, may be represented in the binary CT image 900 (e.g., other bones, medical instruments, etc.). Thus, at step 304b, according to one embodiment, these artifacts may be filtered out of the image. This is beneficial to further simplify the image to represent primarily (or only) the broken fragments that will be later reduced via, for example, surface matching.

Thus, at step 304b, a 2-D connected component labeling (CCL) algorithm, in conjunction with an area filter, may be used to remove (i.e. filter) the unwanted artifacts (which are typically small in size). As is known, a CCL algorithm scans an image and groups the image's pixels into components based on pixel connectivity. That is, the pixels in a connected component may share similar pixel intensity values and are, in some way, connected with each other. Each component may then be separately identified (i.e. labeled). Also, as is known, an area filter may be used to filter out (or include) components having an area value exceeding (or under) a threshold value.

In one implementation, after running the CCL algorithm, connected components with an area less than the threshold value may be deleted from the binary image 900. For example, the threshold value of the area filter can be chosen to be one-thousand pixels, and any individually identified component having a pixel count value less than this is removed from the image. It should be understood that the value of the area filter may be selected based on the size of the image, the size of the bone fragments to be reduced, the type and quantity of artifacts, etc.

Figure 10:
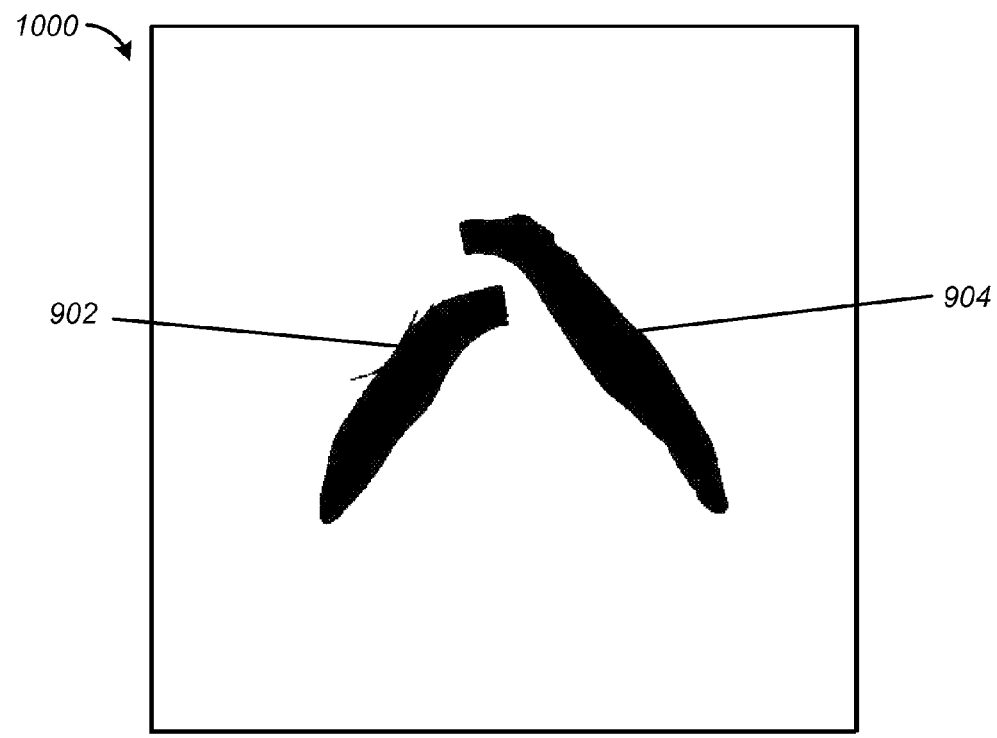
FIG. 10 is a binary image corresponding to the binary image shown in FIG. 9 generated as a result of connected component labeling and size filtering operations performed by the method of FIG. 4.

The result of the processing operations executed in step 304 of FIG. 3 is depicted in the filtered binary image 1000 of FIG. 10. Each of fragments 902 and 904, were identified as components by the CCL algorithm, and thus, were identified as having an area of greater than one-thousand pixels. The artifacts 906 of FIG. 9 were identified as having an area less than one-thousand pixels, and thus, have been removed from the filtered binary image 1000. Each 2-D CT image slice may be processed according to step 304.

At step 306, a three-dimensional (3-D) graphical/volumetric model may be generated from each of the resulting processed two-dimensional CT image slices 900. The model, for example, may be generated by propagating the results of the two-dimensional CCL algorithm along the axial direction, resulting in the identification of the three-dimensional fracture fragments.

At step 308, the virtual surgical system determines the contours of the fragmented/fractured ends of the bone fragments to be reduced in each CT image slice. The contours of the fragmented/fractured ends in the individual CT image slices are collated and represented by a fracture surface data set for each of the fragments. Because the physical surfaces of the corresponding fragmented/fractured ends of bones typically fit together only in a single orientation, these surface data sets may be used to ultimately determine the three-dimensional orientation of the corresponding bone fragments for alignment in the reduction.

In some embodiments, artificial intelligence or other computer algorithms may be incorporated in the virtual surgical system 102 to provide or suggest end-points (and possibly intervening points) corresponding to the contour of the surfaces of the bone fragments. However, in one embodiment, the virtual surgical system 102 uses user-assisted, interactive contour detection to determine the contour of the end points of the fractured bones. That is, user input corresponding to the reconstruction area of the fractured bones is received by the virtual surgical system 102.

Figure 5:
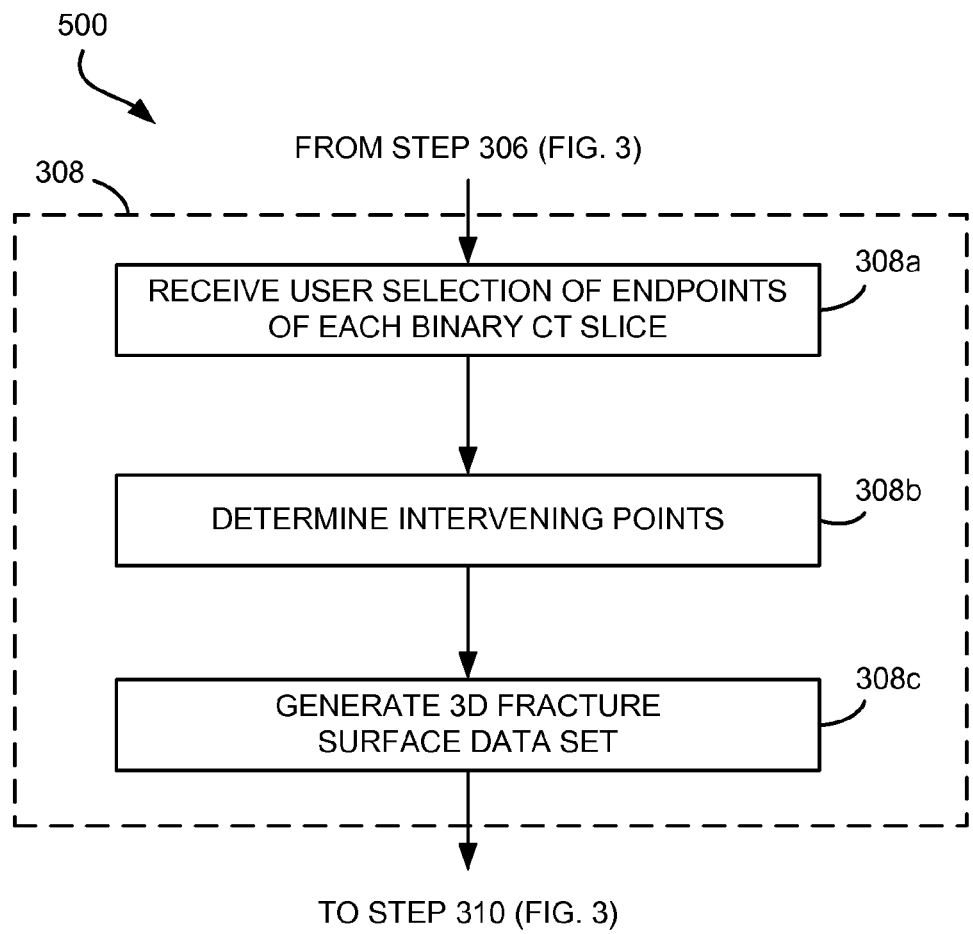
FIG. 5 depicts a flow diagram illustrating one embodiment of a method for selecting fragment contours that may be used with the method of FIG. 3.

FIG. 5 depicts a user-assisted, interactive contour detection embodiment 500, which may be performed to determine the contour as illustrated in step 308 of FIG. 3. At step 308a, a user is iteratively guided through one or more graphical interfaces to select (e.g., via a mouse, stylus, or other input means) end points of a fracture contour in the CT slices. Exemplary user interfaces for the interactive contour detection are described in more detail below with respect to FIGS. 12-14. However, the contour points may be selected, for example, upon the user selection (e.g., a mouse button click, key press, etc.) of a particular area (e.g., a pixel, or group of pixels) according to the position of a cursor (e.g., guided by a mouse or other input device) over the two-dimensional CT scan image. The user performing the selection may, for example, be a surgeon or one skilled in performing such operations. The virtual surgical system 102 collects the data corresponding to the position of these user-selected points.

At step 308b, once the end-points of the fracture contour are selected in each two-dimensional CT slice, the intervening contour points (between the endpoints) may be automatically determined by virtual surgical system 102 at step 308b. For example, the contour points may be generated by system 102 using a contour tracing algorithm. For example, the contour tracing algorithm may be, but is not limited to, a square tracing algorithm, a Moore-neighbor tracing algorithm, radial sweep algorithm, a Theo Pavlidis algorithm, or an active contour fitting using snakes and a Hough Transform.

At step 308c, the contour points, which may include both user-selected end-points and automatically generated intervening points, from the CT image stack (collectively, "three-dimensional fracture surface data") are assembled to generate a three-dimensional fracture surface data set representing the contour of the end surface of the fractured object to be reduced. A three-dimensional fracture surface data set may be generated for each fracture surface (e.g., for each fragment).

Now that each fracture surface is represented by a surface data set, the fragment surfaces can be matched to its corresponding fragment surface. Thus, the surface matching process matches portions of one fragment surface with corresponding portions of another fragment surface. Once these matching areas (e.g., points) are known, a transformation can be determined that will place one fragment surface in registration with the matched surface of the other fragment. The resulting transformation of the surface can be used to position (e.g., by translation and/or rotation) the entire fragment in its pre-fracture alignment with a corresponding fragment.

Accordingly, looking back to FIG. 3, a surface matching process may be implemented by virtual surgical system 102 at step 310. The surface matching process matches the contours of the end surfaces of each bone fragment to determine orientation of each piece such that the broken ends match and fit together for reduction. In one embodiment, the surface matching process can implemented in the virtual surgical system 102 with either, or both of, an iterative closest point (ICP) algorithm and a Data Aligned Rigidity Constrained Exhaustive Search (DARCES) algorithm. For the purposes of illustration of the implemented ICP and DARCES algorithms, the fragment/data set to be matched is denoted as the sample fragment data set and the fragment data set to which the sample fragment data set is to be matched is denoted as the model fragment data set. Each of the ICP and DARCES algorithms may establish a correspondence between the two surface data point sets to be matched, and may also compute a three-dimensional transformation of one or more of the objects to bring the two surface data point sets into registration.

Figure 6:
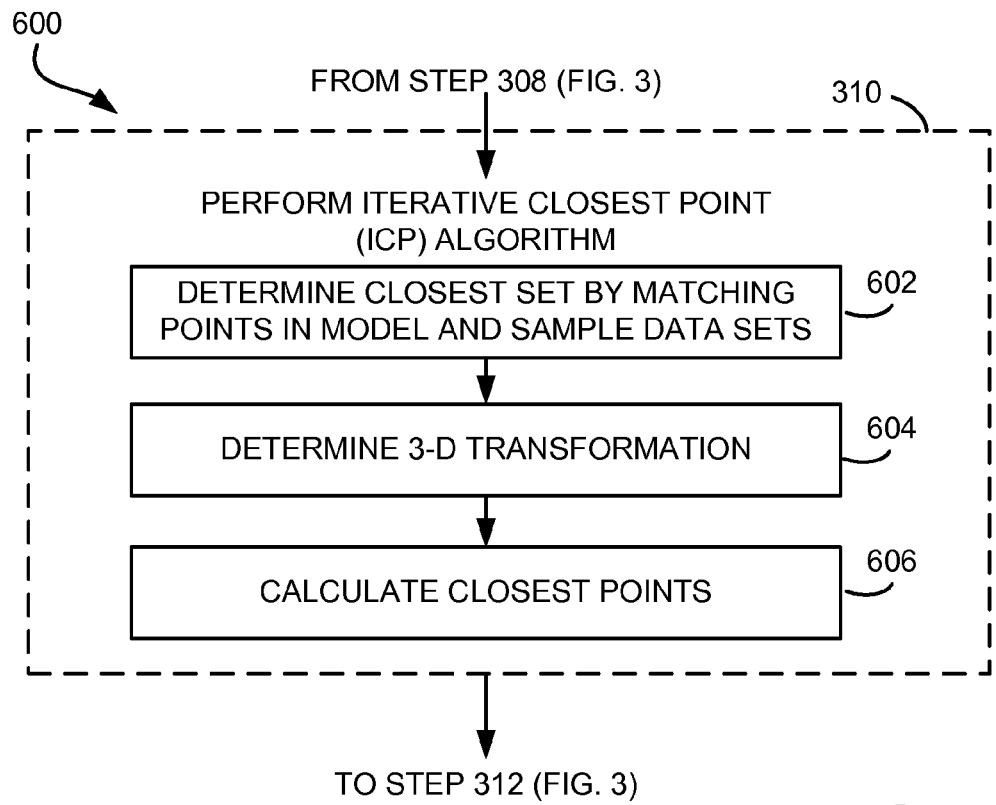
FIG. 6 depicts a flow diagram illustrating one embodiment of an iterative closest point (ICP) algorithm used for surface matching that may be used with the method of FIG. 3.

Looking to FIG. 6, a surface matching algorithm, using ICP process 600 is performed on the sample and fragment data sets. For example, at step 602, the matching points in the model data set corresponding to points in the sample data set are determined. This new set of matching points in the model data set, which represents a subset of the original model data set, is designated as the closest set. Next, at step 604, the three-dimensional rigid body transformation, which may include three-dimensional translation and three-dimensional rotation, that brings the two surfaces into registration (i.e. alignment) is computed. The transformation may, for example, be obtained using the Theory of Quaternions (see, e.g., P. J. Besl and N. D. McKay, "A Method for Registration of 3-D Shapes", *IEEE Trans. Pattern Analysis and Machine Intelligence*, 14(2), 1992, pp. 239-255, herein incorporated by reference). Once calculated, the computed transformation is applied to the original sample fragment data set.

At step 606, the mean squared error (MSE) between the transformed sample data points (from step 604) and the corresponding closest points in the closest set is calculated. The MSE ($\epsilon^2$) is given by:

$$\varepsilon^2 = 1/N \sum_{i=1}^{N} \|c_i - Rs_i + T\|^2 \quad \text{(Eq. 2)}$$

where R denotes the rotation, T denotes the translation, $s_i$ denotes a point of the sample data set and $c_i$ represents the corresponding point in the closest set.

Figure 11:
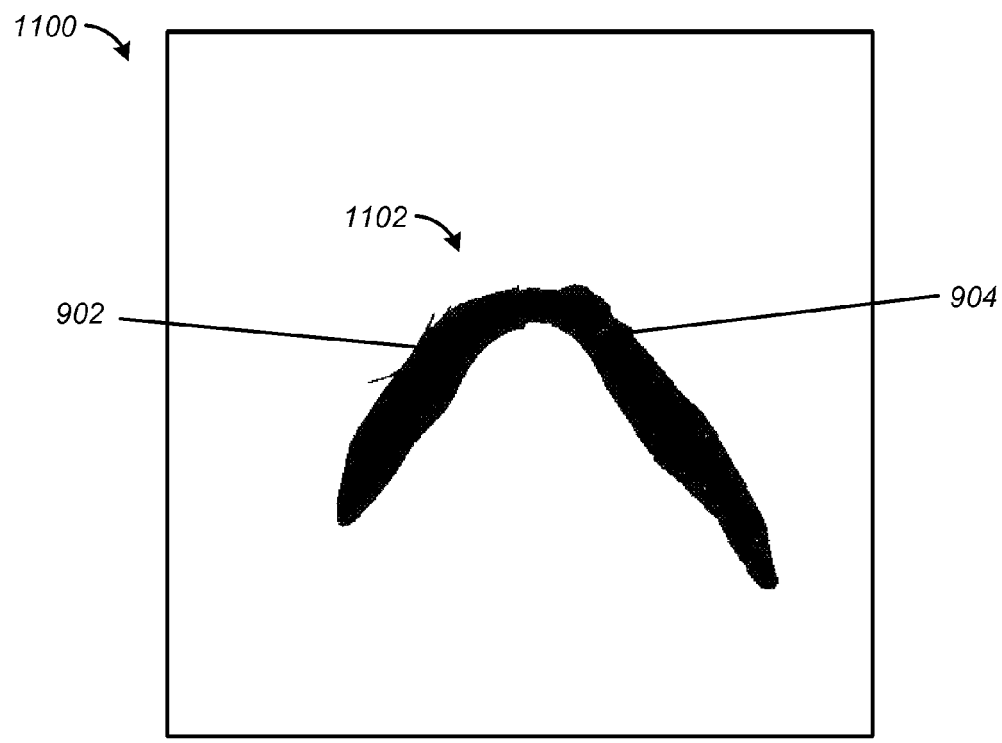
FIG. 11 is a binary image corresponding to the binary image shown in FIG. 10 generated as a result of a three-dimensional surface matching operation.

Steps 602-604 are repeated with an updated sample set (generated by applying R and T obtained at the current iteration to the current sample set) until a pre-specified error convergence criterion is reached. As depicted in FIG. 11, a CT image scan slice 1100 depicts bone fragment 902 after being transformed according to the transformation obtained satisfying the pre-specified convergence criterion. Thus, the resulting reduced bone 1102 comprises bone fragment 902, having been transformed to be aligned with bone fragment 904.

To compute the closest set at step 602, the matching point pairs can be determined using the Maximum Cardinality Minimum Weight Bipartite Matching (MCMW) algorithm based on the Hungarian method proposed by Kuhn (see H. W. Kuhn, "The Hungarian method for the assignment problem," *Nav. Res. Log. Quart.* 2, 1955, herein incorporated by reference).

For a Bipartite Graph G(V, E) with vertex set V and edge set E, the 3-D sample and model data sets correspond to the two disjoint vertex subsets (V1, V2) of the vertex set V. The edge-weight ($W_{ij} \epsilon E$) between any two nodes i and j (such that i$\epsilon$V1 and j$\epsilon$V2) is deemed to be the Euclidean distance between them. Note that the Euclidean distance is invariant to a 3-D rigid body transformation. Thus, the edge weights are given by:

$$W_{ij} = [(x_i - x_j)^2 + (y_i - y_j)^2 + (z_i - z_j)^2]^{1/2} \quad \text{(Eq. 3)}$$

In some embodiments, further enhancements to the MCMW algorithm may be made. For example, the objective function of Eq. 3 may be modified using a reward-penalty scheme to take into account the surface irregularities on the two fracture surfaces. Using a reward/penalty scheme, edge weights ($W_{ij}$) between the two corresponding points i and j in Eq. 3 may be updated by adding a penalty term ($Penalty_{ij}$) to the Euclidean Norm ($Enorm_{ij}$):

$$W_{ij} = Enorm_{ij} + \lambda Penalty_{ij} \quad \text{(Eq. 4)}$$

where $\lambda$ is the penalty coefficient.

In a first approach, the signs of the mean and Gaussian surface curvature are used to classify points on the fracture surfaces into primitive surface categories. Corresponding surface points on the opposable fracture surfaces are rewarded if they belong to compatible surface types, and penalized otherwise.

In a second approach, the surface points are assigned membership values to the two fuzzy sets "bulge" and "droop." Corresponding surface points on the opposable fracture surfaces are rewarded based on their membership values within the same fuzzy set, and penalized otherwise.

Each of these approaches are detailed more specifically in Bhandarkar, S. M., Chowdhury A. S., Tollner, E. W., Yu, J. C., Ritter, E. W., and Konar, A. 2005a. Surface Reconstruction for Computer Vision-based Reconstructive Surgery. *Proc. IEEE Workshop on Applications of Computer Vision (WACV 2005)*, Breckenridge, Colo., Jan. 5-7, pp. 257-262, which is incorporated by reference.

Further, the minimum mean squared surface matching error criterion for optimal reconstruction may be enhanced to include additional shape-based and/or biomechanical stability-based criteria, as described further below. For craniofacial surgery, this additional shape-based and/or biomechanical stability-based criteria may be the 3-D shape symmetry of the reconstructed mandible, maximum smoothness and continuity of the reconstructed mandibular surface and minimum surface strain energy, and the minimum surface area for the reconstructed mandibular surface.

Now that various ICP algorithm embodiments have been discussed, attention is now directed to embodiments of a DARCES algorithm which may be used to perform the surface matching step 310 of FIG. 3. Looking to FIG. 7, DARCES algorithm 700, may be used alone, or in combination with, ICP algorithm 600. DARCES algorithm 700 may be used for solving a partially overlapping three-dimensional surface registration problem efficiently and reliably. It is assumed that one skilled in the art understands the general concepts of implementing DARCES algorithms (see, for example, C. S. Chen, "RANSAC-Based DARCES: A New Approach to Fast Automatic Registration of Partially Overlapping Range Images", *IEEE Trans. Pattern Analysis and Machine Intelligence*, 21(11), 1999, pp. 1229-1234, herein incorporated by reference).

The DARCES method does not require local feature detection and does not require initial transformation estimation for the matching of the two 3-D data sets. Thus, DARCES algorithms differ from any feature-based approach or iterative approach for performing the 3-D surface matching (i.e., 3-D surface registration).

Figure 7:
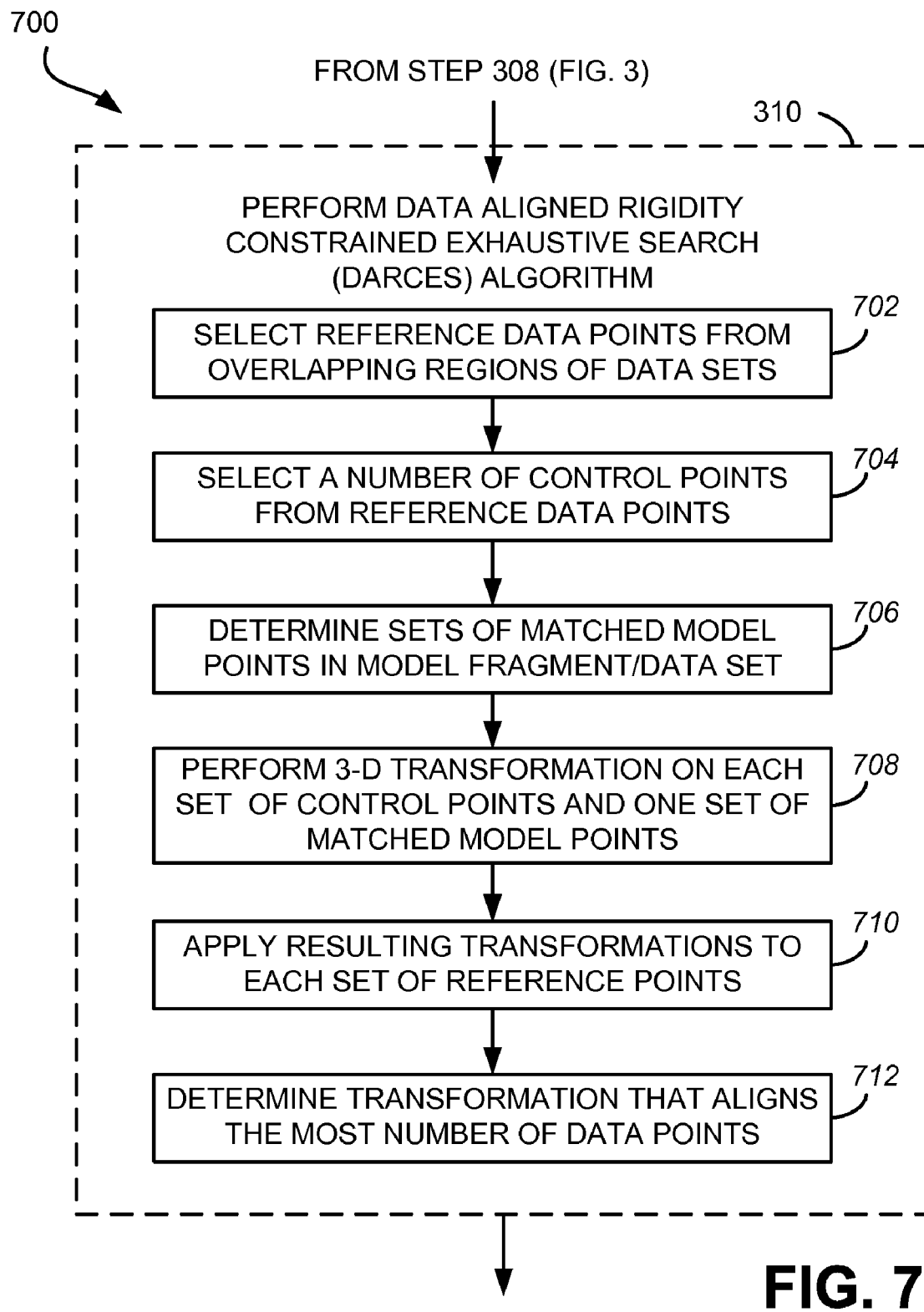
FIG. 7 depicts a flow diagram illustrating one embodiment of a Data Aligned Rigidity Constrained Exhaustive Search (DARCES) algorithm used for surface matching that may be used with the method of FIG. 3.

Looking to FIG. 7, at step 702, reference points are exhaustively selected from the sample data set representing the common set of CT image slices in the CT image stack. The CT images include both the opposable fracture surfaces, represented by the sample data set and the model data set, respectively.

At step 704, a number of control points are chosen from the set of selected reference points. Control points may be described as those that, if matched with corresponding points in the model data set, would enable a three-dimensional rigid body transformation (which may include three-dimensional rotation and three-dimensional translation) to be computed. Control points may be chosen, for example, using an improvised Random Sample Consensus (RANSAC) based approach.

In the present embodiment, for example, three control points are selected. Although three points are selected, in other embodiments, more may be selected. The three control points may be selected according to geometrical constraints. For example, the control points may be selected such that they form an equilateral triangle. According to one embodiment, the length of a side of the triangle may be varied between 25%-35% of the maximum spread of the reference data set. The alignment thresholds are chosen to be different along each coordinate axis. Along each of the x, y, z axes, the alignment thresholds may be chosen to be equal to the respective voxel resolutions.

Once a set of control points are selected from the reference points of the sample fragment data set, at step 706 a set of corresponding three matching points on the model data set (herein, "matched model points") are determined such that they satisfy the same inter-point constraints as the set of three control points. Typically, for the three reference points, there will be a number of such sets of three matched model points in the model fragment data set. Each of these matchings may be enumerated and the best match selected as described below.

At step 708, for each set of three pairs of corresponding points (i.e. each set of three control points and one set of three matched model points), a three-dimensional rigid body transformation is obtained, which may include a translational and rotational component. For determining the rotational component of the three-dimensional rigid body transformation, the Singular Value Decomposition (SVD) technique may be employed (see K. S. Arun, T. S. Huang and S. D. Blostein "Least-Squares Fitting of Two 3-D Point Sets" *IEEE Trans. Pattern Analysis and Machine Intelligence*, 9(5), 1987, pp. 698-700, herein incorporated by reference). Note that three pairs of corresponding points are sufficient to determine a three-dimensional rigid body transformation.

At step 710, each transformation is then applied to all the reference points in the sample fragment data set, other than the three control points. If the distance between a transformed reference point and its nearest matched model point is below a predetermined threshold, then this reference point is considered to have been successfully aligned or matched with the model surface. Thus, the number of successfully aligned sample data points in the sample fragment data set is computed for each transformation. At step 712, the transformation that successfully aligns the most number of sample data points with the model surface data set is deemed to be the solution (e.g., the closest transformation) to the surface matching problem.

Now that ICP and DARCES algorithm approaches have been described that can be used with the virtual surgical system, it is helpful to understand the inherent advantages of each approach. For example, the DARCES algorithm is useful with outlier (e.g., noise or noisy data) rejection, but the resulting three-dimensional rigid body transformation computed by the DARCES algorithm is, in general, not as precise as the ICP algorithm. The ICP algorithm, on the other hand, generally yields a more accurate three-dimensional rigid body transformation but can be sensitive to outliers in the input data. Thus, using the ICP algorithm, the presence of outliers may cause inaccurate computer estimates during the transformation computation process. Moreover, the pairs of matched points generated by the DARCES algorithm also helps in reducing the cardinalities of the two data sets to be matched (using Bipartite Graph Matching) in the ICP algorithm (see N. Christofides, *Graph Theory An Algorithmic Approach*. Academic Press, 1975. pp. 372-379, herein incorporated by reference).

Thus, the dense bipartite graph used to determine the closest set in the ICP algorithm can be reduced to a sparse bipartite graph with fewer nodes and edges (see W. Kim and A. C. Kak, "3-D Object Recognition Using Bipartite Matching Embedded in Discrete Relaxation", *IEEE Trans. Pattern Analysis and Machine Intelligence*, 13(3), 1991, pp. 224-251, herein incorporated by reference). The subsequent MCMW algorithm has a much reduced computational complexity when run on a sparse bipartite graph. Simultaneously, a much lower MSE can be achieved for the matching of the two surfaces, since the DARCES algorithm provides a better starting point to the ICP algorithm by virtue of outlier removal. Thus, the synergetic combination of the DARCES and ICP algorithms, where the inputs to the ICP algorithm are the original model set and the sample set transformed by the DARCES algorithm, results in an improved surface matching algorithm with a substantial reduction in the mean squared error (MSE) (e.g., higher reconstruction accuracy) and reduced execution time for the reconstruction of the craniofacial skeleton.

Figure 8:
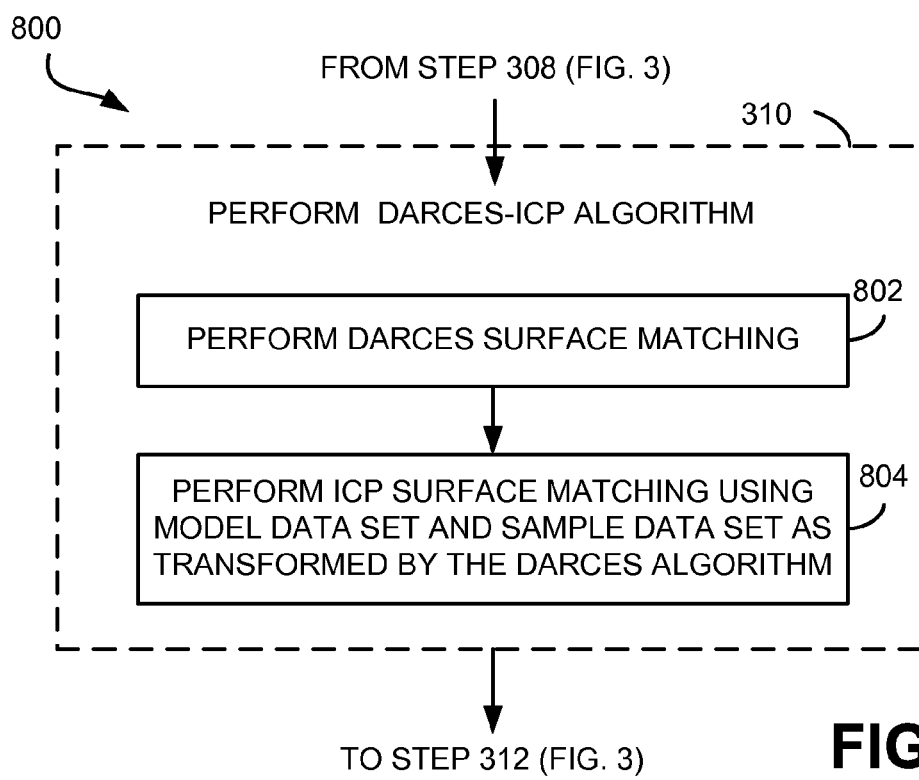
FIG. 8 depicts a flow diagram illustrating one embodiment of a combined ICP-DARCES algorithm used for surface matching that may be used with the method of FIG. 3.

Accordingly, as depicted in FIG. 8, one embodiment of virtual surgical system 102 performs the surface matching step 308 of FIG. 3 using a DARCES-ICP algorithm 800 that, as implied by the name, synergistically includes a combination of the DARCES algorithm and an ICP algorithm. At step 802, the DARCES algorithm is performed (e.g., see FIG. 7) using the sample and model data sets of the original fragmented surfaces. The DARCES algorithm produces a transformed sample fragment data set representing the transformation required to bring the surfaces to their pre-fractured positions.

At step 804, an ICP algorithm (e.g., see FIG. 6) may be performed using the transformed sample data fragment set generated by the DARCES algorithm of step 802. Thus, it may be said that, according to this embodiment, the output of the DARCES algorithm is fed as input to the ICP algorithm.

Evaluations between the surface matching results from the ICP, DARCES and DARCES-ICP algorithms have been performed. Comparison of the MSE metric for the matched surfaces for each of the above algorithms shows that the DARCES-ICP hybrid algorithm yields a lower MSE metric than both the ICP and DARCES algorithms. The DARCES and ICP algorithms are purely data driven. In practice, in addition to obtaining a locally optimal solution, the preservation of the global three-dimensional shape of the human mandible is very much desirable.

Thus, looking back to FIG. 3, at step 312, a visual reconstruction is provided. For the visual reconstruction step, a three-dimensional image of the reconstructed area may be generated. The generated three-dimensional image may, for example, be displayed on display 104, or transmitted to another suitable display, for providing a depiction of the fragmented parts, as reduced to their pre-fracture orientation, according to the surface matching performed at step 310. This three-dimensional visual representation enables a surgeon, or other skilled practitioner, to determine the type and configuration of a prosthesis to use to secure the reduced fragments in place without having to see the actual bone fragments (e.g., after dissection in surgery).

Figure 15:
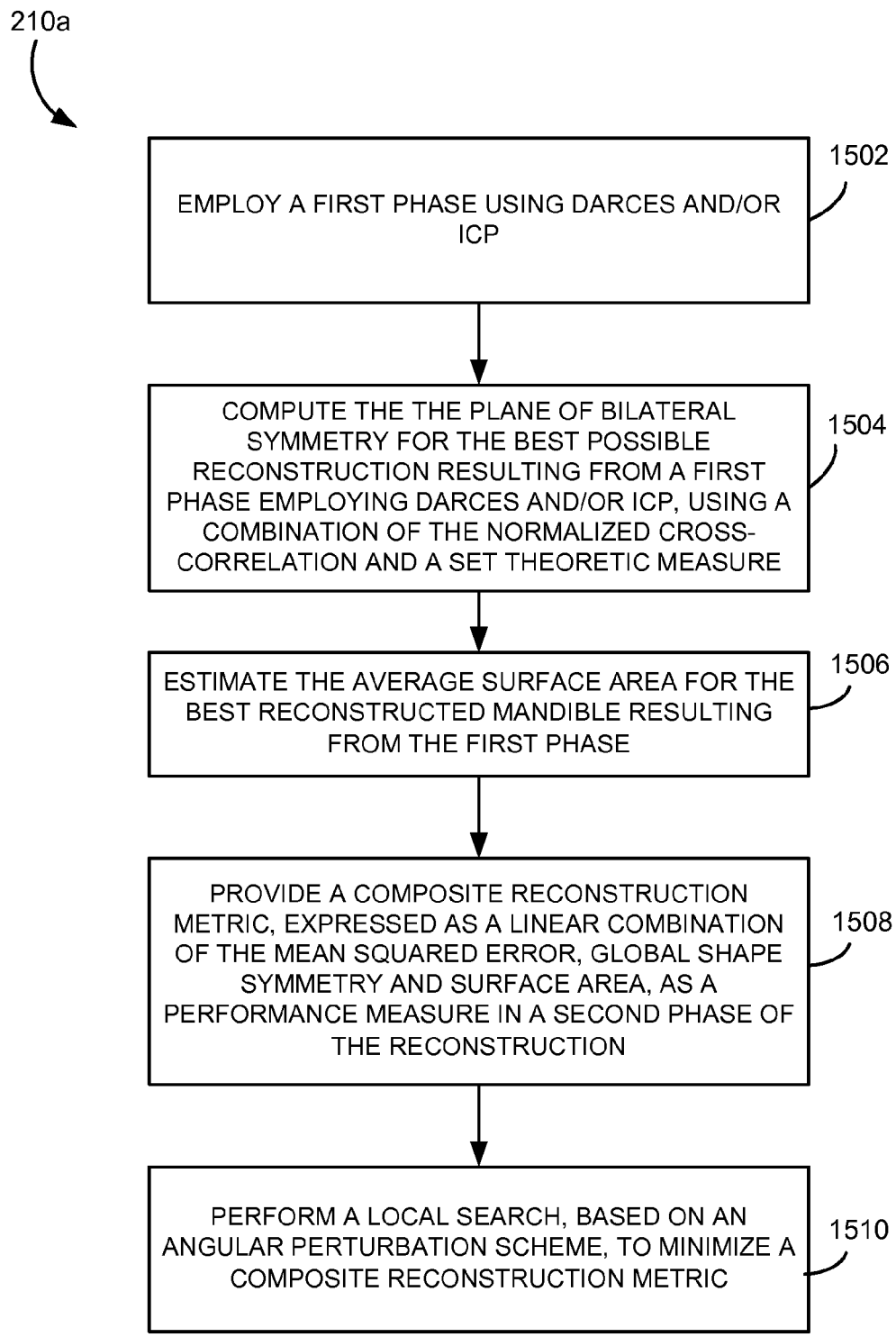
FIG. 15 depicts a flow diagram that illustrates one embodiment of a method employed by an enhanced surface matching module of the virtual surgical system shown in FIGS. 1 and 2.

Having generally described various embodiments of the virtual surgical system 102, the methodology employed by the modules 210-240 of the virtual surgical system 102 are described below. In particular, FIG. 15 shows a flow diagram that illustrates a method embodiment, referred to as method 210a, employed by the virtual surgical system 102 in cooperation with previously described methodology described above in association with FIGS. 3-8. In general, the method 210a employs a two-phase approach in the surface matching process. In the first phase, the ICP and DARCES algorithms are applied first individually and then in a synergistic combination, as explained above (1502). The ICP algorithm solves the 3D correspondence problem using Bipartite Graph Matching. The synergetic combination of the two algorithms, where the output of the DARCES algorithm is fed as an input to the ICP algorithm, is observed to result in an improved surface matching algorithm with a considerable reduction in both, the mean squared error (MSE) and the execution time. In the second phase, it is noted that the anatomy of the human mandible clearly exhibits bilateral symmetry. Furthermore, basic biomechanical principles indicate that the most stable state for a solid body is a state with minimum energy, and this fact should be applicable to the human mandible as well. Since both the ICP and DARCES algorithms are essentially data driven and are purely local in nature, the first phase does not explicitly guarantee the preservation of either the global shape symmetry or the biomechanical stability of the reconstructed human mandible. In the second phase, a composite reconstruction metric is introduced and expressed as a linear combination of three different terms, namely (a) the MSE, (b) a global shape symmetry term and (c) a surface area term (which is shown to be a measure of biomechanical stability). An angular perturbation scheme is used to optimize the composite reconstruction metric. Thus the second reconstruction phase addresses the anatomical shape preservation as well as biomechanical stability issues in the reconstruction paradigm (which may not be always possible in the operating room).

Having described the first phase (1502) above in association with FIGS. 3-8, attention is directed to the second phase. Referring to FIG. 15, step 1504 comprises computing the plane of bilateral symmetry for the best possible reconstruction resulting from the first phase (using ICP and/or DARCES), using a combination of the normalized cross-correlation and a set theoretic measure. To ensure preservation of the global shape of the reconstructed human mandible, the plane of bilateral symmetry is determined for the reconstructed human mandible. For instance, assume the general equation of a three dimensional plane to be:

$$F(x,y,z)=Ax+By+Cz-D=0 \qquad \text{(Eq. 5)}$$

It is known that the planes of reflection symmetry for any rigid body pass through its center of mass and that their coefficients are the components of the eigenvectors of the real symmetric moment of inertia matrix/tensor. This fact allows the determination of the possible candidates for the planes of reflection symmetry without recourse to exhaustive search. The elements of the 3×3 moment of inertia matrix/tensor are the second order centralized moments for the rigid body under consideration. Once the coefficients of the three symmetry planes are determined, the entire mandible is reflected about each of these planes. For each point f(x, y, z) in the reconstructed mandible, there exists a corresponding point $f_R$(x, y, z) in the reflected mandible, given by the following equation:

$$f_R(x, y, z) = \begin{cases} f(x, y, z) - 2\frac{F(f)}{\|\nabla F\|}\frac{\nabla F}{\|\nabla F\|} & \text{if } F(f) > 0 \\ f(x, y, z) + 2\frac{F(f)}{\|\nabla F\|}\frac{\nabla F}{\|\nabla F\|} & \text{otherwise} \end{cases} \qquad \text{(Eq. 6)}$$

where the F is computed using equation (5). There are various measures of symmetry to be found in the existing art, such as the sum of absolute distance and the normalized cross-correlation. One metric used in the method 210a comprises a linear combination of the normalized cross-correlation and a set-theoretic measure. If the reconstructed mandible g and the reflected mandible h are treated as two N-dimensional vectors, the normalized cross-correlation ϒ between g and h is given by:

$$\Upsilon(g, h) = \frac{(g - \bar{g}u)}{\|g - \bar{g}u\|}\frac{(h - \bar{h}u)}{\|h - \bar{h}u\|} \qquad \text{(Eq. 7)}$$

where $\bar{g}$ and $\bar{h}$ are the means of the elements of g and h respectively and u is an N-dimensional unit vector. Alternatively, g and h can be considered as two 3D data sets of cardinality n. A set theoretic term β is introduced as a measure of overlap between the sets g and h:

$$\beta = 1 \frac{|g \Delta h|}{|g \cup h|} \quad \text{(Eq. 8)}$$

where Δ denotes the symmetric difference between and ∪ represents the union of the reconstructed mandible set g and the reflected mandible set h. Note that β lies between 0 (when there is no overlap between g and h) and 1 (when there is perfect overlap between g and h). The proposed metric for global shape symmetry, denoted by GM, is given by:

$$GM = \lambda_1 * \gamma + \lambda_2 * \beta \quad \text{(Eq. 9)}$$

$$\text{where } \sum_{i=1}^{2} \lambda_i = 1 \quad \text{(Eq. 10)}$$

Depending on the problem structure and image representation, different values of $\lambda_1$ and $\lambda_2$ can be chosen. For purposes of discussion, assume $\lambda_1 = \lambda_2 = 0.5$. The plane with the largest value of GM is deemed to be the plane of bilateral symmetry.

Addressing biomechanical stability, and referring to FIG. 15, step 1506 comprises estimating the average surface area for the best reconstructed mandible resulting from the first phase. Minimization of surface area can be shown to be mathematically equivalent to minimization of surface energy and used as a measure of biomechanical stability. For instance, surface energy minimization is modeled along the well accepted principle of strain potential minimization, which, in turn, is based on minimization of the strain energy of an isotropic solid. The strain potential (U) can be defined as follows:

$$U = \iiint_{v} f \begin{pmatrix} \text{normal and shear strains,} \\ \text{Young's and shear } moduli, \\ \text{Poisson ratio} \end{pmatrix} dv \quad \text{(Eq. 11)}$$

Details of the functional form of f for an isotropic solid are known. The normal and shear strains occurring in response to a force field are represented by a displacement field u and resisted by forces arising from the Young's and shear moduli. A body force B (operating on a volume V with surface area S) and surface shear forces T result in a deformation pattern that minimizes U. Further, it can be shown that the following criterion must be satisfied under equilibrium conditions:

$$\iint_{S} T \cdot \delta u \delta a + \iiint_{V} B \cdot \delta u \delta v - \delta U = 0 \quad \text{(Eq. 12)}$$

The integral on the left in equation (12) is a surface energy term. For illustrative purposes, near zero resistance to movement resulting from a force of unity may be assumed. Thus, the energy related to volumetric response is near zero. Hence, it can be concluded that a minimum potential energy state results in minimum surface energy. Further, minimum surface energy in the context of moving fragments with constant surface force is consistent with minimum surface area. So, a biomechanically stable state (e.g., a state with minimum potential energy) is guaranteed, or essentially guaranteed, by a state with minimum surface area. In one embodiment, only the top and bottom curved surfaces (of the six possible surfaces) of the human mandible in a CT image stack (that account for the maximum contribution to the total surface area) are considered. Each surface (S) can be modeled of as an aggregation of disjoint surface patches (SP):

$$S = \bigcup_{i=1}^{n} SP_i \quad \text{(Eq. 13)}$$

$$SP_i \cap SP_j = \phi \text{ if } i \neq j \quad \text{(Eq. 14)}$$

The determinant (gm) of the first fundamental form matrix G for each surface patch can be computed using techniques of differential geometry. The area of each surface (SA), in terms of its constituent surface patch areas (SPA) and metric determinants (gm), is given by the following equation:

$$SA = \sum_{i=1}^{n} gm_i^{1/2} * SPA_i \quad \text{(Eq.15)}$$

where n is the number of surface patches comprising a given surface. Each digital surface (patch) can be approximated by an analytic surface (patch) using, for instance, a least-squares surface fitting technique. Discrete bi-orthogonal Chebyshev polynomials can be used as the basis functions for each such surface patch within an N×N window (where N=5 in an exemplary case). The surface function estimate that minimizes the sum of squared surface fitting error within the window is given by:

$$\hat{f}(u, v) = \sum_{i,j=0}^{3} a_{i,j} \varphi_i(u) \varphi_i(v) \quad \text{(Eq. 16)}$$

where the $\phi_i$'s are the basis functions for the Chebyshev polynomials. Coefficients of the functional approximation are given by:

$$a_{i,j} = \sum_{(u,v)=(-M,-M)}^{(u,v)=(M,M)} f(u, v) b_i(u) b_j(v) \quad \text{(Eq. 17)}$$

where $M=(N-1)/2$ and the $b_i$'s are the normalized versions of the above polynomials. From the estimated coefficients, the first and second order partial derivatives of the fitted surface patch can be computed. These partial derivatives can be used to compute the elements of the first fundamental form matrix G of the fitted surface patch. Finally, the determinant gm of the matrix G for that surface patch can be computed according to known methods.

Referring to step 1508, a composite reconstruction metric, expressed as a linear combination of the mean squared error, global shape symmetry and surface area, is provided as a performance measure in the second phase of the reconstruction. One rationale behind the second phase of the reconstruction scheme, which consists of an angular perturbation scheme, is to arrive at a reconstruction that minimizes the MSE between the matched fracture surfaces and also yields the best possible shape symmetry and biomechanically, the most stable configuration. A normalized composite reconstruction metric (CRM), which is a linear combination of the MSE, the inverse of the global shape symmetry (since the optimization problem is formulated as one of minimization) and the surface area (as a measure of surface energy, which, in turn, determines biomechanical stability) is proposed as a performance measure for the perturbation scheme and is given by:

$$CRM = \alpha_1 * \xi^2 + \alpha_2 * GM^{-1} + \alpha_3 * ((TSA+BSA)/2) \quad \text{(Eq. 18)}$$

where $\xi^2$ is the MSE, GM is given by equation (9), and TSA and BSA denote the top and bottom surface areas respectively and are estimated using equation (15). The $\alpha_i$'s are determined using the following equation:

$$\frac{\alpha_1}{|\partial(\xi^2)|} = \frac{\alpha_2}{|\partial(GM^{-1})|} = \frac{\alpha_3}{|\partial((TSA+BSA)/2)|}; \sum_{i=1}^{3} \alpha_i = 1 \quad \text{(Eq. 19)}$$

where $|\partial(t)|$ denotes the normalized absolute difference (e.g., difference of the maximum and minimum values, divided by the maximum value) of the term t over the range of perturbation. One of the rationales behind model generation is to exploit certain key anatomical measurements to fine-tune the coefficients in the equation (18). These coefficients can be computed based on the normalized absolute differences of the associated factors over the range of angular perturbations.

In step 1510, a local search, based on an angular perturbation scheme, is performed to minimize a composite reconstruction metric instead of just the MSE alone. In one embodiment, perturbations are applied to the fracture site in steps of 0.2° from −1° to +1° about each of the x, y and z axes. In each perturbed state, a new CRM is estimated after re-computing all the three components in equation (18). The small range of angular perturbations is justified based on a reasonable expectation that the locally best (minimum MSE yielding) solution generated by the DARCES-ICP hybrid algorithm is not very far off from the best overall solution (resulting the minimum CRM value). The choice of angular quantization (0.2°) is a judicious compromise between execution time and accuracy. For instance, in at least some implementations, the smaller the angular quantization, the higher the execution time of the algorithm. On the contrary, making the angular quantization too large may prevent the algorithm from arriving at the best possible solution. The state generating the minimum CRM value is deemed to be the desired reconstruction.

The quantitative reconstruction results (e.g., the MSE), obtained by using the various surface matching algorithms (described above) are shown in Table 1. That is, Table 1 below shows a comparison of MSE values obtained by applying various surface matching algorithms. Table 2 below shows a symmetry plane determination for a typical unperturbed state resulting from phase-I of the reconstruction. In other words, Table 2 shows typical values for the parameters $\gamma$, $\beta$ and GM (in the equations (7), (8), and (9) respectively) for the three different candidate symmetry planes in the unperturbed state. The variations of the mean squared error, the inverse global metric for the plane of the bilateral symmetry, the average surface area and the normalized composite reconstruction metric as a function of angular perturbations along all the three major axes can be graphically portrayed, as illustrated in the provisional application from which priority by the present disclosure is claimed, and hence incorporated by reference in its entirety. The ranges of variations for these parameters along with their coefficients in equation (19) are shown in Table 3.

Specifically, Table 3 shows a comparison of the normalized variations of the different terms in eqn. (18) and their coefficients in eqn. (19). As revealed in the tables below, with the incorporation of very small angular perturbations, it is possible to attain a reconstruction state, which not only yields better results in terms of the average surface area and shape symmetry, but also significantly reduces the local MSE. This fact is clearly revealed in Table 4, where the first and the second row respectively show the values of different terms of equation (18) for the unperturbed configuration (e.g., the reconstruction generated by the hybrid DARCES-ICP algorithm) and the optimal configuration (for a perturbation of −0.4° about the x-axis, yielding the minimum normalized CRM value). That is, Table 4 shows a comparison of the performance measures associated with the optimal state (−0.4° rotation about x-axis) and the unperturbed state (the MSE, Inverse_GM, Average Surface Area and CRM values are all normalized). These results show the effectiveness of the second phase of the proposed virtual reconstruction.

TABLE 1

| Surface Matching Scheme | MSE (mm²) |
|---|---|
| ICP | 0.91 |
| DARCES | 0.33 |
| Hybrid DARCES-ICP | 0.25 |

TABLE 2

| γ | β | GM | Equation of the Plane | Comment |
|---|---|---|---|---|
| 0.79 | 0.88 | 0.83 | 0.98x − 0.16y + 0.12z = 65.42 | Plane of Bilateral Symmetry |
| 0.27 | 0.72 | 0.50 | −0.20x − 0.87y − 0.45z = 58.78 | — |
| 0.35 | 0.82 | 0.59 | −0.03x + 0.47y + 0.88z = 50.95 | — |

TABLE 3

| | MSE | Inverse Global Symmetry | Average Surface Area |
|---|---|---|---|
| Variations | 0.86 | 0.07 | 0.12 |
| Coefficients | 0.82 | 0.06 | 0.11 |

TABLE 4

| Axis | Angle | MSE | Inverse_GM | Average Surface Area | CRM |
|---|---|---|---|---|---|
| x | −0.4° | 0.138 | 0.952 | 0.892 | 0.275 |
| — | — | 0.148 | 0.964 | 0.982 | 0.293 |

Note that although the above results are based on phantom data sets, the reconstruction paradigm, using the statistically robust RANSAC-based DARCES algorithm revealed by the various method embodiments described above, is adequate to handle the issue of outliers and missing data in case of real data sets. The hybrid DARCES-ICP algorithm may provide an accurate reconstruction (with lower MSE) followed by the second reconstruction phase to guarantee a minimum CRM value on real data sets. In some embodiments, a model-guided feedback may be applied to fine-tune the coefficients of the different terms in the composite metric in equations (18) and

(19) to result in an even better reconstruction. Further, though described in the context of a single fracture reconstruction framework, some embodiments may be extended to multiple fractures using a combinatorial optimization approach.

In some embodiments, the virtual surgical system 102 may incorporate, in part or in whole, expert system technology (e.g., artificial intelligence) to provide a three-dimensional image of the reconstructed area together with a recommended prosthesis or prostheses for joining, for example, the fractured bone fragments. In other words, some embodiments of the virtual surgical system 102 may suggest, for example, any of one or more types of prostheses, the configuration of the prosthesis (e.g., what the prostheses should look like), a proposed location of the prostheses with respect to the reduced bone fragments, and how the prostheses should be used.

Now that the general functionality of the virtual surgical system has been described, attention is now directed to a number of graphical user interfaces which may be used to implement various functionality of the virtual surgical system. The graphical user interfaces may, for example, be displayed on display 104 (FIGS. 1-2) and provide an interface between a user and the virtual surgical system 102.

Figure 12:
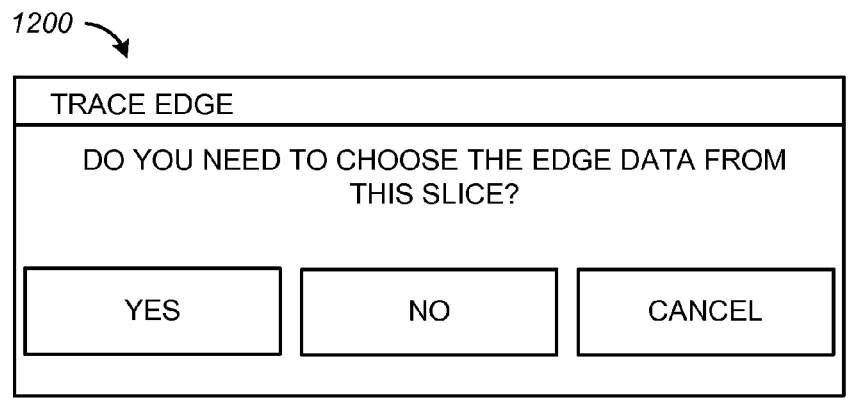
FIGS. 12-14 depict embodiments of graphical user interfaces for enabling a user to cooperate with the virtual surgical system of FIG. 1 to extract surface contour data from each CT image scan slice.

Looking to FIG. 12, a graphical user interface 1200 depicts a first interface displayed during the interactive contour detection process of step 308a of FIG. 5. Graphical user interface 1200 requests a user's decision as to whether edge data (e.g., contour endpoints of a fragmented object) should be collected from a particular image slice. After user interface 1200 is displayed, the user may respond by selecting a YES button icon, a NO button icon, or a CANCEL button icon. If the user response is No, the interface program fetches the next binary CT image slice and asks the same question. If the answer is Cancel, the current functionality is forcibly aborted. If the user responds Yes, the interface of FIG. 13 may be displayed.

Figure 13:
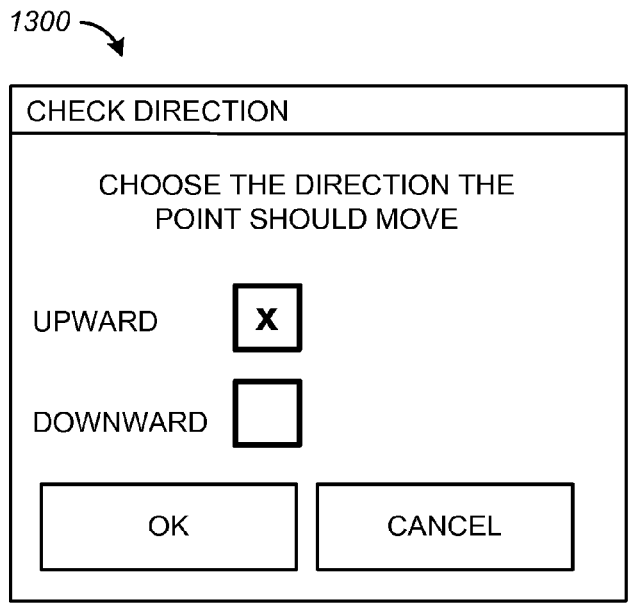

FIG. 13 depicts a menu 1300 used to select end-points of a contour fracture of one of the broken fragments via, for example, a mouse click. The menu screen in FIG. 13 provides the user the needed flexibility in the event that the mouse clicks are not accurate enough. Thus, after selecting a point on the image with the mouse, the user can specify a direction (by checking the UPWARD or DOWNWARD option, for example) in which the clicked point needs to be adjusted in order to provide more precise selection of the edge point on the fracture contour. Although only an upward-downward adjustment is provided in the embodiment of FIG. 13, it should be understood that a left and/or right adjustment may also be provided, and the menu may be modified and customized according to a users requirements. The user presses the OK button to proceed.

Figure 14:
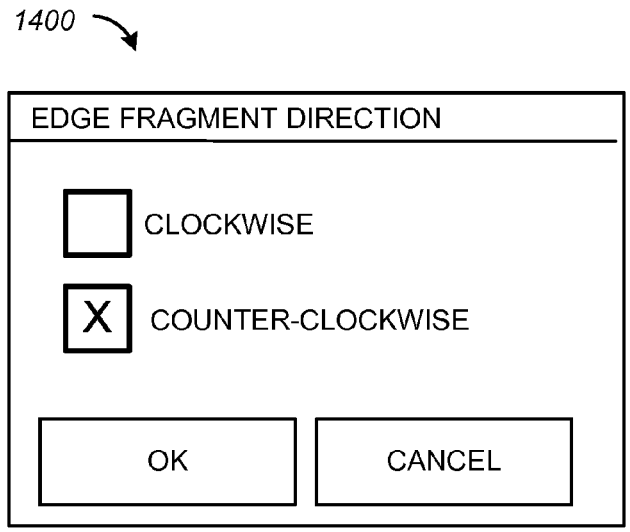

Once the reference points (i.e., the topmost and bottommost points) along the fracture contour are determined using menu 1300 of FIG. 13, the user may specify the contour tracing direction (e.g., step 308b of FIG. 5) namely, CLOCKWISE or COUNTER-CLOCKWISE using the menu depicted in FIG. 14. Once the fracture contour is traced in the specified direction, the user may presses the OK button to permit the data acquisition for the binary CT image slice under consideration. Once the surface data acquisition from one fracture fragment from all the slices is completed, the same process can be repeated for the other broken fragment(s).

In some embodiments, automation may be implemented in lieu of, or in addition to, the various user interface approaches described above. Introducing automation in various aspects of reconstructive surgery is a highly demanding and technically challenging task, employing techniques from various diverse disciplines such as computer vision, graph theory, and statistics to automatically detect stable fracture points in CT image sequences of a fractured human mandible. As set forth above, one approach of processing a sequence of 2D CT image data is a computationally efficient alternative to processing the 3D volume data directly. The fracture surface data, which comprises input to the above-described virtual reconstruction algorithms, were thus far explained as an extraction by the mechanism of surgeons manually identifying the stable fracture points in the CT image sequence. In some implementations, such manual identification can be a performance bottleneck in the overall virtual reconstruction process, especially when dealing with complex multiple fractures. In certain embodiments described below, detection of stable fracture points is automated, which can improve the speed and accuracy of the overall virtual craniofacial reconstruction.

Figure 16:
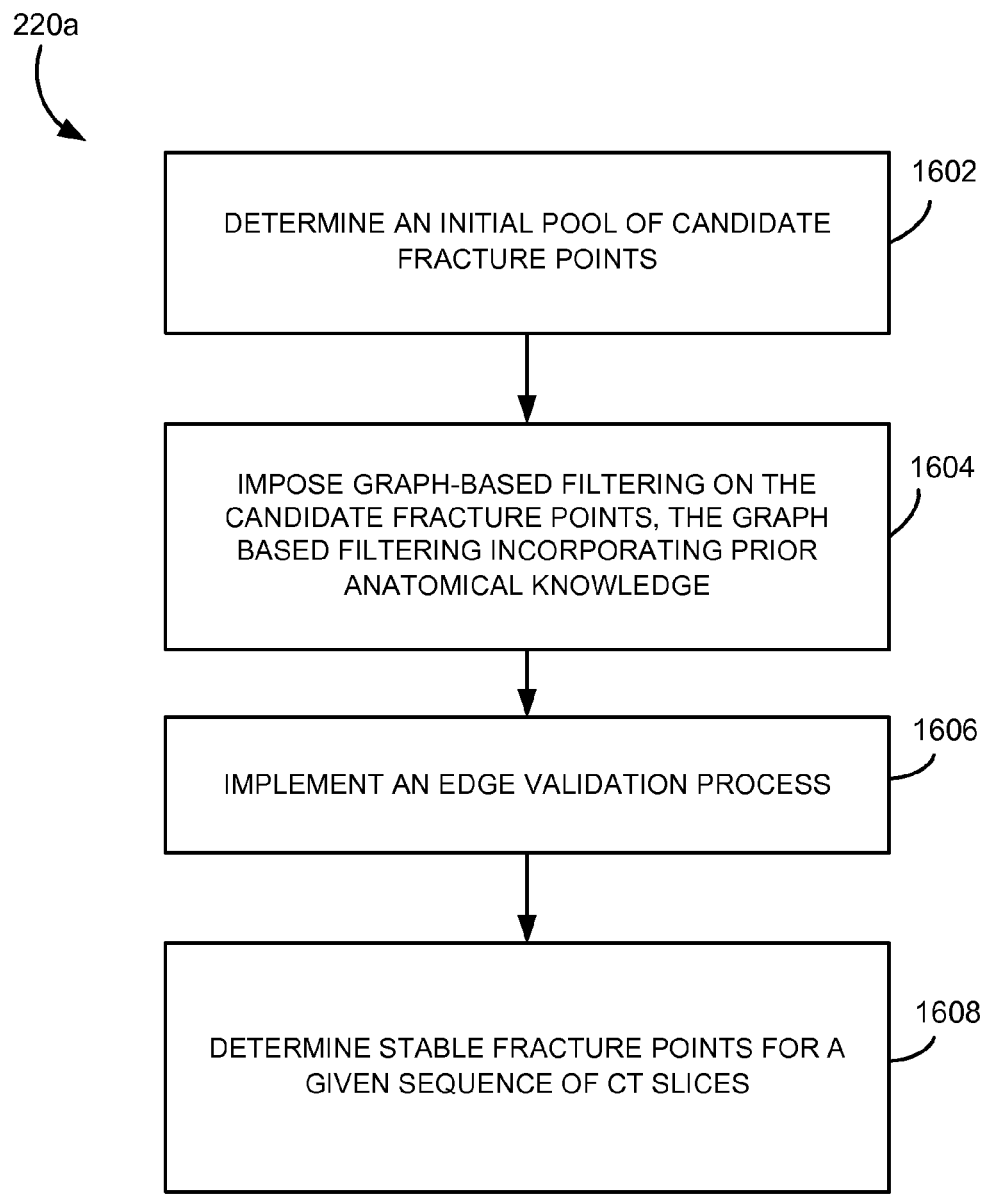
FIG. 16 depicts a flow diagram that illustrates one embodiment of a method employed by an auto-fracture detection module of the virtual surgical system shown in FIGS. 1 and 2.

Following the CT image slice procedures explained above, the automated fracture detection module 220 employs a process or method, referred to as method 220a in FIG. 16, that detects fracture points (which are essentially corners or points of high curvature in the individual 2D CT image slices) based on concepts from curvature scale-space theory and graph theory. In particular, step 1602 comprises determining an initial pool of candidate fracture points. Let |EL| be the total number of edge pixels of a component in any 2D CT slice where each edge pixel is represented as a 2D array element EL[i], having coordinates EL[i].x and EL[i].y. Let k be the number of forward and backward edge pixels used to determine whether or not pixel i is a potential corner; $\phi_{ij}$ the angle between any two edge pixels i and j; and θ the threshold angle for corner determination. The following algorithm, based on curvature scale space theory, can be used to determine a potential corner:

```
for i: 1 -> |EL|
    for m: 1 -> k
    Find
```
$$\varphi_{i+m,i-m} = \tan^{-1}\left(\frac{EL[i+m] \cdot y - EL[i-m] \cdot y}{EL[i+m] \cdot x - EL[i-m] \cdot x}\right);$$
```
    end for;
    if
mark pixel i as a potential fracture point;
    end if;
end for;
```

The complexity of the algorithm is $O(c \cdot k \cdot |EL|)$, where c is the number of components.

Having determined the candidate fracture points or corners, step 1604 comprises imposing graph-based filtering on the candidate fracture points, the graph based filtering incorporating prior anatomical knowledge. That is, with the corner points as vertices and the edges between vertices weighted by the Euclidean distance between them, an undirected weighted graph, denoted by G=G(V, E) is constructed. Listed below are the properties of G:

(1) |V| is the initial set of corners obtained using curvature scale-space theory. Thus each vertex is essentially a point in 2D space.

(2) The edges are deemed to exist only between successive vertices, e.g., |E|=|V|−1.

(3) The edge weights are given by the Euclidean distances (|| ||) between the corresponding vertices:

$$E[i][j] = \begin{cases} \|V_i - V_j\| & j = (i \% |V|) + 1 \\ 0 & \text{otherwise} \end{cases} \quad \text{(Eq. 20)}$$

where % denotes the modulo operator.

If two vertices in the constructed graph G=G(V, E) are spatially very close, then from prior anatomical knowledge, it can be concluded that the vertices cannot form the starting and terminating points of a fracture contour. So, a subgraph $G_1=G_1 1V_1, E_1$) is constructed using what is referred to herein as a vertex condensation procedure, which essentially coalesces two closely spaced vertices. The complexity of the condensation process is O(|E|). As the contours of a component under consideration is traced digitally, the possibility of incurring an error in the computation of the angle and the distance between two closely spaced vertices, as set forth below, can be quite large. Thus the vertex condensation procedure, when performed before distance and/or angle computation, provides more accuracy.

Step 1606 comprises implementing an edge validation process, where all the edges of the subgraph $G_1$ are checked and only those edges which satisfy the following two constraints are retained according to the following methodology:

(a) The absolute value of the angle $\phi_i$ between the two vertices i and j, given by:

$$\varphi_{ij} = \tan^{-1}\left(\frac{V_1[i] \cdot y - V_1[j] \cdot y}{V_1[i] \cdot x - V_1[j] \cdot x}\right) \quad \text{(Eq. 21)}$$

is constrained to lie within a pre-specified range:

$$\phi_{ij} \in [\phi_{min}, \phi_{max}] \quad \text{(Eq. 22)}$$

b) The edge weight $E_1[i][j]$, which is the Euclidean distance between two vertices i and j, is constrained to lie within a pre-specified range:

$$E_1[i][j] \in [l_{min}, l_{max}] \quad \text{(Eq. 23)}$$

From prior anatomical knowledge of the fracture edge lengths and orientations, all $\psi_{min}, \psi_{max}, l_{min}, l_{max}$ can be determined. Computation of $\phi_{ij}$, $E_1[i][j]$ and checking their bounds can be performed individually in O(1) time. Since this computation and checking is to be done for each edge in $G_1$, the total complexity of this part is O(|$E_1$|) and that of the entire graph based filtering is O(|E|)+O(|$E_1$|), which is linear in the number of edges. The overall complexity of the two-phase corner (fracture point) detection process (using curvature scale-space theory and graph theory) for each CT slice is given by:

$$O(c.k.|EL|)+O(|E|)+O(|E_1|). \quad \text{(Eq. 24)}$$

Successive 2D CT slices of a given 3D object can be considered as being observed at successive time instants. Hence, step 1608 determines stable fracture points for a given sequence of CT slices. For instance, one goal is to track the various fracture points along successive 2D CT slices and develop a mathematical notion of spatial consistency. One approach described below is to use a Kalman filter with a Bayesian perspective. The basic measurement and state equations at time t are given by the following linear stochastic difference equations respectively:

$$X_t = AX_{t-1} + w_t \quad \text{(Eq. 25)}$$

$$Z_t = HX_t + v_t \quad \text{(Eq. 26)}$$

where $X_t \in \Re^2$ is the actual state or parameter vector, $Z_t \in \Re^2$ is the measurement or observation of the velocity or (rate of) change of position of a fracture point in successive CT image slices. Assume both the process noise ($w_t$) and measurement noise ($v_t$) is to be normally distributed with zero mean and constant variance Q and R respectively. Thus $$p(w) \sim N(0,Q) \quad \text{(Eq. 27)}$$

$$p(v) \sim N(0,R) \quad \text{(Eq. 28)}$$

A further assumption is that the estimation/prediction of the velocity or change in position along both the axes is mutually independent. Thus in the present case, Q and R are diagonal 2×2 matrices. Additionally, an assumption is made that A and H are 2×2 identity matrices. Under the assumption that the initial state vector X is normally distributed with mean $\mu_0$ and variance $\Sigma_0$, the following definition is proposed:

$$\mu_{t-1} = E[X_{t-1} | \hat{Z}_{t-1}] \quad \text{(Eq. 29a)}$$

$$\Sigma_{t-1} = \text{var}[X_{t-1} | \hat{Z}_{t-1}] \quad \text{(Eq. 29b)}$$

$$\hat{Z}_{t-1} = [Z_1, \ldots, Z_{t-1}] \quad \text{(Eq. 30)}$$

From equations (25)-(30) at any time t, the distribution of the state vector is normal with parameters [26-27]:

$$E[X_t | \hat{Z}_{t-1}] = \mu_{t-1} \quad \text{(Eq. 31a)}$$

$$\text{var}[X_t | \hat{Z}_{t-1}] = \Sigma_{t-1} + Q \quad \text{(Eq. 31b)}$$

The expected new observation has a normal distribution, with parameters:

$$E[Z_t | \hat{Z}_{t-1}] = \mu_{t-1} \quad \text{(Eq. 32a)}$$

$$\text{var}[Z_t | \hat{Z}_{t-1}] = \Sigma_{t-1} + Q + R \quad \text{(Eq. 32b)}$$

When a new observation $Z_t$ is made, the parameter vector $X_t$ is updated according to the Bayes' rule:

$$p(X_t | \hat{Z}_t) \propto p(Z_t | X_t) p(X_t | \hat{Z}_{t-1}) \quad \text{(Eq. 33)}$$

Thus the posterior is normal with parameters:

$$E[X_t | \hat{Z}_t] = \mu_{t-1} + KF_t(Z_t - \mu_{t-1}) \quad \text{(Eq. 34a)}$$

$$\text{var}[X_t | \hat{Z}_t] = (\Sigma_{t-1} + Q)(\Sigma_{t-1} + Q + R)^{-1} R \quad \text{(Eq. 34b)}$$

where the Kalman Filter Gain $KF_t$ at time t is given by:

$$KF_t = (\Sigma_t + Q)(\Sigma_t + Q + R)^{-1} \quad \text{(Eq. 35)}$$

The spatial consistency for a particular fracture point is first checked in individual CT image slices (starting, for instance, with the second slice). For this purpose, a high posterior density (HPD) prediction interval (or similar mechanisms, such as one based on parametric shape estimation) is constructed for the posterior distribution. Since the HPD prediction interval is developed at the same level of statistical significance $\alpha$, for two independent directions x and y, Bonferroni's procedure is employed to detect the actual level of significance. This is given by:

$$\alpha' = \alpha/2 \quad \text{(Eq. 36)}$$

The two-sided 100(1−$\alpha$) % HPD prediction intervals for the x and y directions are respectively given by:

$$E\left[X_{1t} | \hat{Z}_{1t}\right] \pm \left(z_{\alpha'/2} * \sqrt{\left(\text{var}\left[X_{1t} | \hat{Z}_{1t}\right]\right) + R_{11}}\right) \quad \text{(Eq. 37)}$$

-continued $$E[X_{2t}|\hat{Z}_{2t}] \pm \left(z_{\alpha'/2} * \sqrt{(\text{var}[X_{2t}|\hat{Z}_{2t}]) + R_{22}}\right) \quad \text{(Eq. 38)}$$

where the value of $z_{\alpha'/2}$ can be obtained from the standard normal table. Let the HPD prediction intervals at any time instance t+1 along the two directions be $HPD_{1t}$ and $HPD_{2t}$, and the corresponding observations be $Z_{1t+1}$ and $Z_{2t+1}$ respectively. Then a fracture point is deemed as spatially consistent at time point (t+1) if the following condition is satisfied:

$$Z_{1t+1} \epsilon HPD_{1t} \text{ and } Z_{2t+1} \epsilon HPD_{2t} \quad \text{(Eq. 39)}$$

Each time instant in the present context actually corresponds to a CT image slice in a given CT image sequence. A particular fracture corner is deemed as stable or spatially consistent for a given image sequence, if it is detected and determined to be spatially consistent for most of the CT slices in the sequence. Let n be the total number of slices in a given image sequence, m be the number of slices in which a particular fracture point is observed and p be the number of slices in which the fracture point is found to be spatially consistent. Then, a new term S is introduced to denote a measure of stability or spatial consistency for the entire image sequence as follows:

$$S = 0.5((m/n)+(p/n-1)) \quad \text{(Eq. 40)}$$

The maximum value of S is 1. So, a fracture point having a value of S very close to unity is deemed a stable fracture point for the given CT image sequence.

As to the performance benefits, Tables 5 and 6 provide some insight. Table 5 illustrates the total number of fracture points obtained across all the 2D CT slices in a given image sequence by applying various techniques. Table 6 illustrates a value of S for the first six (6) potential corners for a given CT image sequence using 99% and 95% HPD prediction intervals. In general, a total of 472 potential fracture points were obtained using traditional curvature scale-space theory on a CT image sequence of a fractured human mandible. By applying the first round of filtering, based on vertex condensation, about 53% of the potential fracture points were eliminated (as observed in Table 5). In the second phase of filtering using edge length and edge orientation, a further 49% (approximately) of the potential fracture points were eliminated (Table 5). In order to finally locate the stable or spatially consistent corners, it was observed, using the definition of spatial consistency (equation (39)), that at most six (6) fracture points appear consistently across the various CT slices, though not all of the 6 fracture points were anatomically found to be correct. Finally, the stability measure (equation (40)) was used to determine the stable fracture points for the given CT image sequence. The corners were enumerated as 1 through 6 from left to right and top to bottom in a 2D CT image slice. The first 4 corners were deemed to be stable for the given CT image sequence as they yielded values of S close to unity using 99% and 95% HPD prediction intervals (Table 6). Table 5 and 6 are as follows:

TABLE 5

| Scheme | # of fracture points |
| --- | --- |
| Curvature Scale-space | 472 |
| Vertex Condensation | 250 |
| Edge-based filtering | 123 |

TABLE 6

| Corner No. | S (with 99% HPD) | S (with 95% HPD) |
| --- | --- | --- |
| 1 | 0.93 | 0.90 |
| 2 | 0.92 | 0.90 |
| 3 | 0.85 | 0.85 |
| 4 | 0.84 | 0.82 |
| 5 | 0.05 | 0.05 |
| 6 | 0.05 | 0.05 |

In some embodiments, bivariate analysis may be employed for spatial consistency checking. Further, though described in the context of a single fracture, some embodiments may employ the extended Kalman filter and particle filter in more complex multi-fracture scenarios.

Figure 17:
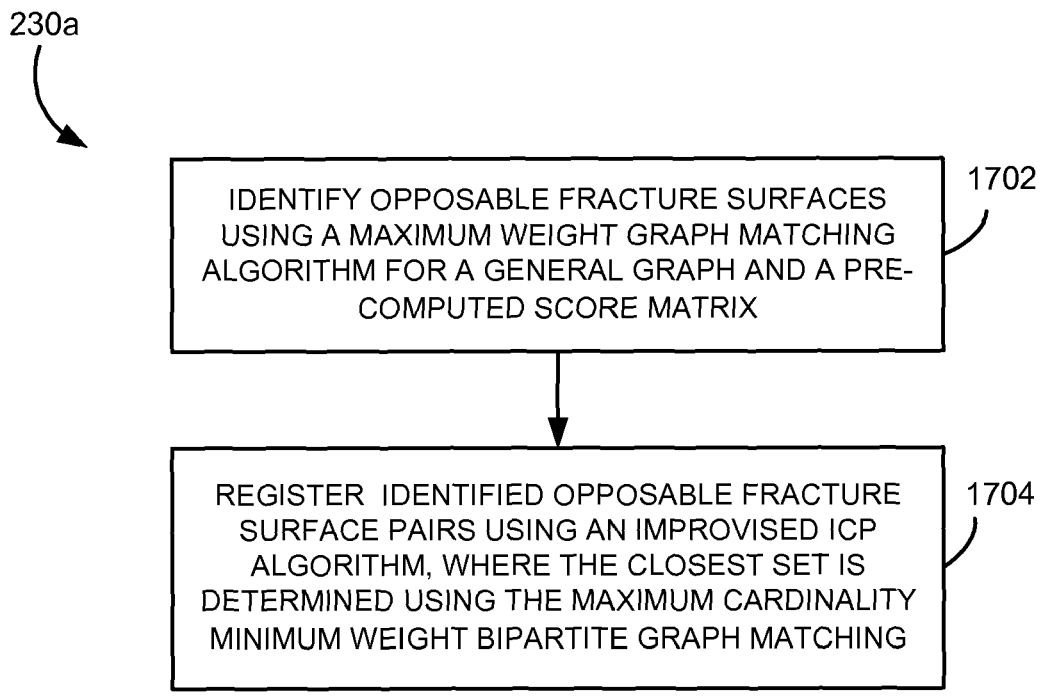
FIG. 17 depicts a flow diagram that illustrates one embodiment of a method employed by a multi-fracture detection module of the virtual surgical system shown in FIGS. 1 and 2.

Having placed an emphasis on single fracture application, attention is now directed to the use of virtual surgical system embodiments in the context of multi-fracture scenarios. Referring to FIG. 17, the multi-fracture module 230 of the virtual surgical system 102 employs, in one embodiment, a two-step solution for the virtual multi-fracture reconstruction, which can also be easily extended in the context of this disclosure to similar problems in different domains. Referring to FIG. 17, step 1702 comprises identifying opposable fracture surfaces using a maximum weight graph matching algorithm for a general graph and a pre-computed score matrix. In step 1704, the already identified opposable fracture surface pairs are registered using an improvised ICP algorithm, where the closest set is determined using the maximum cardinality minimum weight bipartite graph matching. The reconstruction in this second step is constantly monitored using two simple but useful constraints based on the Tanimoto coefficient and concepts of volumetric matching.

Attention is first directed to the formulation of a score matrix of step 1702. As explained above, the input to the system is a sequence of CT images showing broken human mandibles. A score matrix is constructed based on the appearance of various mandible fragments in the input sequence. The mandible fragments are pre-classified as terminals and non-terminals, based on the presence or absence of condyles (a craniofacial body part that exhibits pronounced sphericity) respectively. For simplicity, an assumption is made that a terminal fragment can have one fracture surface while a non-terminal fragment can have two such surfaces, with the understanding that the principles described herein may be extended to handle any number of fracture surfaces for a given fragment. As is known, score matrix formulation in two-dimensional problems, where the matrix elements denote matches between possible opposable edges, is based on curve matching. However, the match score between various 3D fracture surfaces from the CT scan needs to be estimated. A higher matching score is assigned to a fracture surface pair if:

i) the fracture surface pair are found to be spatially proximal, or ii) the fracture surface pair are found to exhibit opposable or complementary fracture surface characteristics. Both of these factors may be used for determining the score.

Since different fracture surfaces have a different number of data points, the notion of a distance (as a measure of spatial separation) between any such pair engenders an establishment of correspondence, which can be computationally quite expensive. To reduce the complexity, a directed Hausdorff distance is employed for this purpose, which does not need any prior correspondence between two data sets to give a measure of spatial separation between them. The Hausdorff distance H(A, B) between two data sets A and B is given by:

$$H(A,B) = \max(h(A,B), h(B,A)) \quad \text{(Eq. 41)}$$

where h(A, B) denotes the directed Hausdorff distance between the two data sets A and B and is given by:

$$h(A,B) = \max_{a \in A} \min_{b \in B} \|a-b\| \quad \text{(Eq. 42)}$$

and $\|a-b\|$ represents the Euclidean distance between the points a and b. Each such a, b in the present case is a 3D data point in the fracture surface data set A and B, respectively. The computation of the Hausdorff distance can be done in O(mn) time where m and n respectively denote the cardinalities of the two fracture surface data sets.

Each fracture surface is essentially a collection of several fracture contours. For each surface, an ordering of the contour curvature appearing in various slices constituting the fracture surface is developed. The choice of contour curvature as a measure of surface irregularity can be guided by the fact that such a choice possesses rotational and translational invariance. The contour curvature for a point (x, y) in a given slice (a specific value of z) is given by:

$$c(x, y) = \frac{\frac{d^2 y}{dx^2}}{\left(1 + \left(\frac{dy}{dx}\right)^2\right)^{3/2}} \quad \text{(Eq. 43)}$$

A score function FS(A, B) for a pair of fracture surfaces A and B is the sum of the fuzzy score fs(a, b) for each possible point pair, one from each surface. If the two points under consideration have the same signs for their curvatures, then they cause the overall score for the surface to increase; otherwise they cause it to decrease. The score function is formally given by:

$$FS(A,B) = \sum\sum fs(a,b) \quad \text{(Eq. 44)}$$
$$a \in A \ b \in B$$

The fuzzy score between a pair of points can be high under the following conditions:
(i) If the slice-wise locations of two points are spatially close;
(ii) If the ordered values/enumerations of the two points in respective slices are close; or
(iii) If the curvature values of two points are close in value.
The score is low if any of the above factors are not satisfied. Mathematically fs(a, b) is the product of the above three factors and is given by:

$$fs(a,b) = S(a,b)E(a,b)C(a,b)sg(c_a c_b) \quad \text{(Eq. 45)}$$

where $$S(a,b) = 2/(1+\exp(|s_a - s_b|)) \quad \text{(Eq. 46)}$$

$$E(a,b) = 2/(1+\exp(e_a - e_b)), \quad \text{(Eq. 47)}$$

$$C(a,b) = 2/(1+\exp(|c_a - c_b|)), \quad \text{(Eq. 48)}$$

Here S(a, b), E(a, b) and C(a, b) respectively denote the slice-wise, enumeration value-wise and curvature value-wise scores of the two points a and b and $s_a(s_b)$, $e_a(e_b)$, $c_a(c_b)$ respectively denote the slice value (e.g., z-value) enumeration of the point in the slice and contour curvature value (given by equation (43)) of the point a (b). Also sg(x) is the sign function, returning 1 if x>0, 0 if x=0, and −1 if x<0. Each of the functions in equation (46), (47) and (48) is designed to capture the prominent variations of the corresponding component terms. Each term has its absolute value in the interval of 0 to 1, and thus satisfies the criterion to be a fuzzy function, except for the sign.

The final score SC(A, B) between two surfaces A and B is given by a linear combination of the inverse Hausdorff distance and surface matching score:

$$SC(A,B) = \lambda_1 H^{-1}(A,B) + \lambda_2 FS(A,B) \quad \text{(Eq. 49)}$$

The less the actual Hausdorff distance (e.g., the more the inverse value), the better is the chance of the surfaces being opposable. Similarly, the greater the surface matching score value, the better is the chance of the surfaces to be opposable. The coefficients of linear combination are determined using following equations:

$$\lambda_1 + \lambda_2 = 1.0 \quad \text{(Eq. 50)}$$

$$\frac{\lambda_1}{\sigma(H^{-1}(A, B))} = \frac{\lambda_2}{\sigma(FS(A, B))} = \frac{\lambda_1 + \lambda_2}{\sigma(H^{-1}(A, B)) + \sigma(FS(A, B))} \quad \text{(Eq. 51)}$$

In eqn. (51), $\sigma(H^{-1}(A, B))$ and $\sigma(FS(A, B))$ respectively denote the standard deviation of $H^{-1}(A, B)$ and FS(A, B) for all possible fracture surface pairs A and B.

In the section that follows, the combinatorial nature of the virtual craniofacial reconstruction problem is illustrated. Then, maximum weight graph matching algorithm is presented as a solution to the combinatorial problem. With an assumption that a non-terminal fragment has two fracture surfaces and a terminal fragment has one fracture surface, the number of possible reconstruction options rcn where n is the total number of fragments is easily seen to be:

$$rc_n = (n-2)! 2^{n-2} \quad \text{(Eq. 52)}$$

With n total fragments, the n−2 non-terminal fragments can be encountered in any of (n−2)! possible orderings. Further, each nonterminal fragment can be oriented so that either of the fracture surfaces is the first in the sequence. This gives the factor $2^{n-2}$ in counting the possibilities. It is clear from the equation (52) that the reconstruction problem is combinatorial in nature.

In literature, this type of combinatorial reconstruction problem may be framed as the well-known traveling salesman problem (TSP). However, the TSP by itself is an NP-complete problem and even the best case solution, which involves incorporation of some heuristics, is factorial in nature. In contrast, the embodiments presented herein model the problem as a maximum weight matching problem for a general graph, where the fracture surfaces are modeled as the vertices of a general graph G and the entries of the score matrix are assigned the various edge-weights between the corresponding vertices. Such a graph matching algorithm has a polynomial time solution (with a time complexity of $O(n^4)$, where n is the number of vertices). The k best solutions are obtained, where k≧2 and solutions are indexed by j (j=1 . . . k). Each solution is a set of unordered opposable fracture surface pairs.

Let $W_j$ denote the sum of the edge-weights for the current best solution and $W_{j+1}$ denote the sum of the edge-weights for the next best solution. Then solution sets are continually generated until the following condition is violated:

$$W_j - W_{j+1} < pW_j \quad \text{(Eq. 53)}$$

where p is an appropriately chosen positive fraction. Hence, a clear way to regulate the generation of the number of solution sets is achieved.

Referring now to step 1704, the fracture surface pairs are registered using an improved ICP algorithm in the second step of the overall reconstruction problem. The main steps of such an improvised ICP algorithm are described below:

(a) The matching points in one fracture surface data set, called the model data set, corresponding to points in the other fracture surface data set, called the sample data set, are determined and termed as the closest set. The matching point pairs are determined using the maximum cardinality minimum weight matching algorithm for a bipartite graph. The use of this algorithm obviates any need for prior alignment of the two fracture surface data sets. The sample and model data sets correspond to the two disjoint vertex sets $V_1$ and $V_2$ (possibly with different cardinalities) respectively in the bipartite graph $G_B$ ($V_1 \cup V_2$, E). The edge-weight ($W_{ij} \in E$) between any two nodes i and j (such that $i \in V_1$ and $j \in V_2$) is deemed to be the Euclidean distance between them. Note that the Euclidean distance is invariant to a 3D rigid body transformation. Thus, the edge weights are given by:

$$W_{ij} = [(x_i - x_j)^2 + (y_i - y_j)^2 + (z_i - z_j)^2]^{1/2} \quad \text{(Eq. 54)}$$

(b) The computed transformation is applied to the original sample data set and the mean squared error (MSE) between the transformed sample data points and the corresponding closest points is computed. The MSE ($\epsilon^2$) is given by:

$$\varepsilon^2 = \left(1/N \sum_{i=1}^{N} \|c_i - (Rs_i + T)\|^2\right) \quad \text{(Eq. 55)}$$

where R denotes the rotation matrix, T the translation vector, $s_i$ a point of the sample data set and $c_i$ the corresponding point in the closest set. Steps (a)-(b) are repeated with an updated sample set (generated by applying R and T obtained at the current iteration to the current sample set) until a pre-specified error convergence criterion (for instance, 0.001 in the present case) is reached.

As described above, the k best possible solution sets are obtained from the maximum weight graph matching algorithm, with commencement of the actual registration of the fracture surface pairs with the best solution set (using the ICP algorithm). After each pair of fracture surfaces are registered, the global shape of the partially reconstructed mandible is monitored using a measure of volumetric overlap with the reference unbroken mandible. In the context of volumetric matching, the Tanimoto coefficient $TC_{f,g}$ between two volumetric shapes f and g is defined as:

$$TC_{f,g} = \frac{O_{f,g}}{I_f + I_g - O_{f,g}} \quad \text{(Eq. 56)}$$

where $$I_f = \iiint f^2(\hat{x}, \hat{y}, \hat{z}) dv \quad \text{(Eq. 57)}$$

$$I_g = \iiint g^2(\tilde{x}, \tilde{y}, \tilde{z}) dv \quad \text{(Eq. 58)}$$

$$O_{f,g} = 2 \iiint f(\hat{x}, \hat{y}, \hat{z}) g(\tilde{x}, \tilde{y}, \tilde{z}) dv \quad \text{(Eq. 59)}$$

Here, $(\hat{x}, \hat{y}, \hat{z}) = (x - x_{RC}, y - y_{RC}, z - z_{RC})$ where $(x_{RC}, y_{RC}, z_{RC})$ is the geometric center of the reference mandible R. Similarly, $(\tilde{x}, \tilde{y}, \tilde{z}) = (x - x_{SC}, y - y_{SC}, z - z_{SC})$, where $(x_{SC}, y_{SC}, z_{SC})$ is the geometric center of the reconstructed mandible S. Then:

$$f(\hat{x}, \hat{y}, \hat{z}) = \begin{cases} 1 & \text{if } (\hat{x}, \hat{y}, \hat{z}) \in R \\ 0 & \text{otherwise} \end{cases} \quad \text{(Eq. 60)}$$

$$g(\tilde{x}, \tilde{y}, \tilde{z}) = \begin{cases} 1 & \text{if } (\tilde{x}, \tilde{y}, \tilde{z}) \in S \\ 0 & \text{otherwise} \end{cases} \quad \text{(Eq. 61)}$$

Then, two volumetric matching based shape constraints are introduced for monitoring the global correctness of the reconstruction: i) With the registration of each fracture surface pair, the value of the $TC_{f,g}$ should always increase. ii) In the present reconstruction scenario, since S is a subset of R, ideally, the overlapped volume $O_{f,g}$ at each stage should be exactly twice the volume of the partially reconstructed mandible $I_g$. This can be seen from equations (57)-(59) with the fact that the volume of the reference mandible $I_f$ always remains constant. The correctness criterion is then defined as:

$$(2I_g - O_{f,g}) \leq (2qI_g) \quad \text{(Eq. 62)}$$

where q is an appropriately chosen positive fraction. If at any point in the reconstruction stage either of the two constraints is violated, the current solution set is abandoned and a fresh reconstruction is commenced with the next best solution set.

As to performance, input CT image sequence had six broken human mandible fragments with a total of ten fracture surfaces. The two fracture surfaces belonging to the terminals were numbered as 1 and 10 and the remaining eight fracture surfaces of the nonterminal fragments were numbered from 2 to 9. Table 7 below shows the extreme values of the Hausdorff distance, the surface match function and the overall score among all possible fracture surface pairs. Table 8 shows results from the graph matching algorithm. Table 9 shows the results of shape monitoring ($A = (2I_g - O_{f,g})/2I_g$).

TABLE 7

| Score Parameter Extremes | Value | Fracture Surface Pair |
| --- | --- | --- |
| Min. Hausdorff distance | 29.83 | (5, 6) |
| Max. Hausdorff distance | 185.12 | (1, 9) |
| Min. Surface Match | −413.39 | (4, 9) |
| Max Surface Match | 955.55 | (1, 4) |
| Min. Overall Score | 1 | (4, 9) |
| Max. Overall Score | 1362 | (1, 4) |

The surface match values are shifted so that the minimum value is 1.0 before using them in eqn. (49) to ensure all positive weights for the general graph. The overall score elements are also rounded to their nearest integer values for the graph matching algorithm. For the present image sequence, the surface match clearly dominates the overall score. However, for a different CT image sequence with fairly similar fracture surface characteristics, the spatial proximity of the fracture surfaces can easily be more decisive. This justifies the inclusion of the Hausdorff distance term in the overall score.

TABLE 8

| Solution Set (j) | $W_j$ |
| --- | --- |
| {(1, 4), (2, 5), (3, 6), (7, 8), (9, 10)} | 4987 |
| {(1, 3), (2, 9), (4, 6), (5, 7), (8, 10)} | 3123 |

Table 8 shows the solution set obtained from the maximum weight graph matching algorithm along with the sum of the edge weights for each solution set. As an example, p=0.1 was chosen, and hence the process was stopped after obtaining two best solution sets according to equation (13).

TABLE 9

| Various Stages of Reconstruction | $TG_{f,g}$ | A |
|---|---|---|
| (1, 4) registered | 1.08 | 0 |
| {(1, 4), (2, 5)} registered | 1.47 | 0 |
| {(1, 4), (2, 5), (3, 6)} registered | 1.57 | 0 |
| {(1, 4), (2, 5), (3, 6), (7, 8)} registered | 1.69 | 0 |
| All 5 fracture surface pairs registered | 21.71 | 0.0003 |

Table 9 describes the results of step-by-step shape monitoring of the partially reconstructed mandible at various stages of its reconstruction. At each stage, both shape constraints (as defined above) are satisfied with a choice of q=0.01. Thus, the best solution set is continued to complete the registration of all five fracture surface pairs.

Thus, the approach described above to the multi-fracture craniofacial reconstruction problem is based on the computation of the score matrix, use of a polynomial time algorithm for solving the combinatorial pattern matching problem, use of an improvised ICP algorithm, and formulation of shape based constraints using concepts of volumetric matching.

Figure 18:
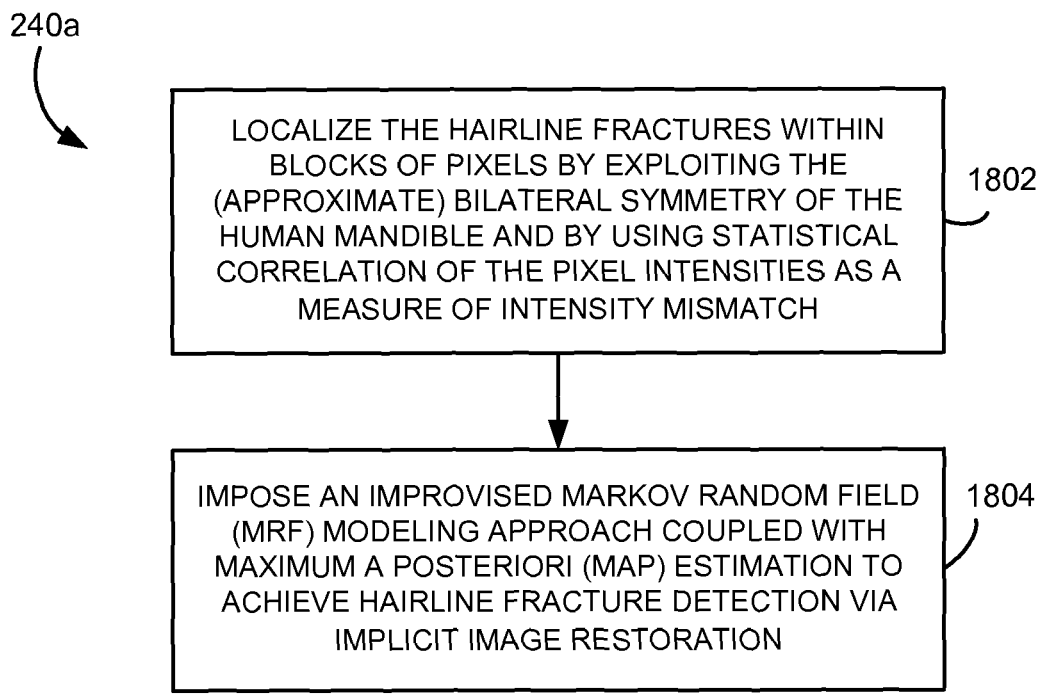
FIG. 18 depicts a flow diagram that illustrates one embodiment of a method employed by a hairline-fracture detection module of the virtual surgical system shown in FIGS. 1 and 2.

Another reconstruction problem addressed by certain embodiments of the virtual surgical systems and methods involves the detection of hairline fractures, as illustrated by the method 240a shown in FIG. 18 (as implemented by the hairline fracture detection module 240). The phrases "hairline fracture" or "minor fracture" generally refer to those situations where the broken bone fragments are not visibly out of alignment. In the presence of noise, the detection and subsequent visualization of hairline fractures is a clinically challenging task. From the perspective of computer vision and pattern recognition research, the problem of detection of hairline or minor fractures in X-ray or CT images is inherently challenging. For instance, conventional techniques for detecting points of surface discontinuity (which are typically based on corner detectors such as the Harris detector) typically do not perform well because of the pronounced intensity inhomogeneity and noise present in X-ray or CT images. Moreover, visual comparison of an Xray or CT image of a mandible with a hairline fracture with that of an unbroken (intact) mandible generally reveals changes in pixel intensity only in the vicinity of the fracture site, resulting in the formulation of an image restoration problem with a mathematically unknown local degradation. This is in sharp contrast to the more conventional image restoration problem with a mathematically known global degradation as outlined by Geman and Geman in their classical paper using Markov random field (MRF) modeling with Maximum A Posteriori (MAP) estimation.

One hairline detection approach of the virtual surgical systems is based on Markov random field (MRF) modeling and Gibbs sampling. Such a hairline fracture detection approach is additionally capable of target pattern generation (e.g., such a method can predict how a jaw with a hairline fracture would appear if allowed to heal naturally without explicit surgical intervention), which has potential prognostic significance because surgeons can use this to help decide if open surgical reduction and fixation is indicated or the fractures can be managed by allowing them to heal spontaneously based on what the spontaneously healed mandible will be like.

In one embodiment, the hairline fracture detection approach of the virtual surgical systems and methods takes as input a stack of 2D CT image slices of the human mandible with one or more hairline fractures and implements the following approach. In step 1802, the hairline fractures are approximately localized within blocks of pixels by exploiting the (approximate) bilateral symmetry of the human mandible and by using statistical correlation of the pixel intensities as a measure of intensity mismatch. In step 1804, within each of the above pixel blocks, an improvised Markov random field (MRF) modeling approach coupled with Maximum A Posteriori (MAP) estimation is imposed to achieve hairline fracture detection via implicit image restoration. That is, the classical MRF-MAP paradigm is improvised to deal with an unknown local degradation of image pixel intensities at the fracture site. This is in contrast to the classical MRF-MAP paradigm which incorporates a global and known deformation model. Further, the classical MRF-MAP paradigm has not been previously applied to the problem of fracture detection in medical images (X-ray or CT) in general.

In particular, the MRF-MAP paradigm handles input noise in an explicit and efficient manner. The approximate localization of fractures within pixel blocks in the first phase or step is shown to result in significant computational savings in the second phase since the MRF modeling and MAP estimation in the second phase, which involves Gibbs sampling, is restricted only to those pixel blocks in the CT image stack which are known to contain potential fractures.

The input to the proposed fracture detection scheme is a stack of 2D CT image slices of the human mandible with a hairline fracture. Each 2D CT image slice is assumed to be parallel to the xy plane whereas the z axis is assumed to be the axial direction along which the CT image slices are acquired. The CT image stack is divided into a number of pixel blocks. The theoretical framework of the two-phase fracture detection and localization scheme is described as follows.

Different anatomical structures within the human body are known to possess different types of symmetry. With regard to step 1802, the (approximate) bilateral symmetry exhibited by the human mandible is exploited. In the case of a hairline fracture, since the bone fragments are not visibly out of alignment, the bilateral symmetry is still preserved to a great extent. The general equation of the 3D plane of bilateral symmetry is given by:

$$Ax+By+Cz=D \quad \text{(Eq. 63)}$$

For an axial CT scan of the human mandible, B and C are assumed to be approximately equal to zero, and the mandibular cross-section to be approximately centered within each CT image slice of width W. Thus, the approximate plane of bilateral symmetry is reduced to:

$$x=W/2 \quad \text{(Eq. 64)}$$

For every incident pixel $g_i$ with coordinates (x, y, z) in the left half of the mandible with a hairline fracture, a bilaterally symmetric pixel $g_i^R$ with coordinates ($x^R$, $y^R$, $z^R$) can be determined as:

$$x^R=W-x, y^R=y, z^R=z \quad \text{(Eq. 65)}$$

Two heuristics are exploited to reduce the search space for coarse fracture localization. These heuristics along with their justifications (based on domain knowledge) are as follows: (a) Since mandibles are essentially bone structures that typically exhibit higher intensity values in CT images, pairs of pixel blocks with high average intensity are sought. This approach helps to remove pixel blocks containing artifacts and/or large amounts of soft tissue from further consideration; (b) The mandible is typically larger in size compared to other bones in the CT images of the craniofacial skeleton. Since a primary focus in on the detection of mandibular fractures, a second round of filtering is performed by applying the connected component labeling algorithm, at the pixel block level rather than at the level of individual pixels, and eliminating components which span only a small number of pixel blocks.

By using the above heuristics, only a few (say q) pixel blocks are retained which are deemed to constitute solely the fractured mandible. Having localized the mandible in the CT image, the next goal is to localize the hairline fracture site within it. This is done by taking a block from the left half of the image, all of whose pixels have x coordinate values: $0 \leq x \leq W/2$, and a corresponding bilaterally symmetric block in the right half of the image, all of whose pixels have x coordinate values $W/2 \geq x \geq W$, and computing the statistical correlation between the two. The correlation coefficient between a typical incident block g, with individual pixels $g_i$. and its bilaterally symmetric counterpart $g^R$, with corresponding pixels $g_i^R$ is given by:

$$r(g, g^R) = \frac{1}{(n-1)} \sum_{i=1}^{n} \frac{(g_i - \bar{g})}{(s_g)} \frac{(g_i^R - \bar{g}^R)}{(s_g^R)} \quad \text{(Eq. 66)}$$

where $\bar{g}$ and $\bar{g}^R$ denote the mean and $s_g$ and $s_g^R$ denote the standard deviation of the pixels within the blocks g and $g^R$ respectively.

Having obtained a value of $r(g,g^R)$ for each pair of pixel blocks $(g,g^R)$, the pixel block pairs are sorted in increasing order of their $r(g,g^R)$ values. Note that the pixel block within the intact (unbroken) half of the mandible has more pixels with higher intensity values (due to the presence of more bone material) compared to its bilaterally symmetric counterpart, which contains the hairline fracture (resulting in some loss of bone material). Thus, one underlying rationale is that pairs of pixel blocks which potentially contain fractures should exhibit a higher intensity mismatch and hence lower correlation values. The user can then choose the best k out of q pixel blocks as sites containing potential hairline fractures.

The above technique for coarse fracture localization provides at least the following two benefits: (1) it achieves computational efficiency by effectively reducing the image size over which the MRF-MAP scheme coupled with Gibbs sampling is to be applied. Thus, instead of applying the proposed MRF-MAP scheme over the entire CT image slice, it is only applied over the select k pixel blocks in each CT image slice. (2) it renders the prior shape information in each CT image slice more relevant and more accurate. Instead of determining two quadratic polynomials to describe the inner contour and outer contour of the entire mandible, there exists only the need to determine the quadratic polynomials that describe the inner and outer contours of the portion of the mandible that appears within each of the selected k pixel blocks.

Attention is now directed to the description of a model according to step 1804. Assume an image with m×n pixels. Let p=m×n. The pixel intensities in the image can be expressed as:

$$g = \Phi(f) + \epsilon \quad \text{(Eq. 67)}$$

where g, f, and ε are p×1 vectors such that g represents the vector of all observed image intensities, f represents the vector of intensities corresponding to the true image, and ε is zero-mean random Gaussian noise, where $$\epsilon \sim N(0, \sigma^2 I_p) \quad \text{(Eq. 68)}$$

and where $I_p$ is the p-th order identity matrix. The function Φ(.) in equation (67) denotes a known degradation (or perturbation) function. Furthermore, it is assumed that the true pixel intensity f has a known prior distribution. The conditional autoregressive model (CAR) is one of several typical prior distributions used extensively in the domain of image processing. The CAR model also ensures the Markovian property of the mean of the prior distribution. Therefore, $$p(g \mid f) \propto \exp\left\{-\frac{1}{2\sigma^2} \|g - \Phi(f)\|^2\right\} \quad \text{(Eq. 69)}$$

$$p(f) \propto \exp\left\{-\frac{1}{2\tau^2} f^T (I_p - \gamma N) f\right\}$$

where N is the neighborhood matrix given by $N=[n_{i,j}]$ such that $$n_{i,j} = \begin{cases} 1 & \text{if } i \text{ and } j \text{ are neighbors} \\ 0 & \text{otherwise} \end{cases} \quad \text{(Eq. 70)}$$

The value of γ is chosen appropriately to avoid singularity of the matrix $(I_p - \gamma N)$. Under this formulation, the posterior distribution of f given the observed data g can be shown to be Gibbsian on account of conjugacy under linear degradation.

In the context of hairline fracture detection, it is assumed that the image of the fractured mandible is a degraded version of some true (perhaps hypothetical) intact mandible. Consequently, the degradation function needs to be formulated in a manner such that if it is applied to the entire true image (e.g., the CT image of the intact mandible), the resulting image displays a hairline fracture at the desired site while retaining the pixel intensity values of the true image everywhere else. Radiologically speaking, a hairline fracture denotes a loss of bone mass and hence a decrease in the Hounsfield unit (image intensity) at the fracture site. Thus, from equation (67), a simple formulation of the degradation function could be $$g = Af + \epsilon \quad \text{(Eq. 71)}$$

where A is the degradation matrix of order p×p consisting of non-zero elements only along the diagonal. For the i-th pixel, $$g_i = a_i f_i + \epsilon_i \quad \text{(Eq. 72)}$$

where $$\alpha_i = \begin{cases} \alpha_i & \text{if } i \text{ is a fracture site} \\ 1 & \text{otherise} \end{cases} \quad \text{(Eq. 73)}$$

for some known $\alpha \in (0,1)$.

The following lemmas may be advanced:

Lemma 1: For each fixed value of g, the posterior probability p(f|g) is a Gibbs distribution with energy function:

$$U(f \mid g) = \frac{1}{2\sigma^2} \|g - Af\|^2 + \frac{1}{2\tau^2} f^T (I_p - \gamma N) f$$

Further, $f_{i-}$ denotes the neighborhood of $f_i$.

Lemma 2: Based on the MRF formulation in equations (68) and (71)-(73), if it is assumed $E(f_i)=\mu(f_{i-})$ then the posterior distribution of $f_i$ given $g_i$ can be shown to be:

$$f_i \mid g_i, f_{i-} \sim N\left(\frac{\frac{a_i g_i}{\sigma^2} + \frac{\mu(f_{i-})}{\tau^2}}{\frac{a^2}{\sigma^2} + \frac{1}{\tau^2}}, \frac{1}{\frac{a^2}{\sigma^2} + \frac{1}{\tau^2}}\right).$$

As a proof of the above, the posterior distribution of $f_i | g_i, f_{i-}$ can be expressed as:

$$p(f_i \mid g_i, f_{i-}) \propto \exp\left\{-\frac{1}{2\sigma^2}(g_i - a_i f_i)^2 - \frac{1}{2\tau^2}(f_i - \mu(f_{i-}))^2\right\}$$

$$\propto \exp\left[-\frac{1}{2}\left\{\left(\frac{a^2}{\sigma^2} + \frac{1}{\tau^2}\right)f_i^2 - 2f_i\left(\frac{a_i g_i}{\sigma^2} + \frac{\mu(f_{i-})}{\tau^2}\right)\right\}\right]$$

$$\propto \exp\left\{-\frac{\frac{a^2}{\sigma^2} + \frac{1}{\tau^2}}{2}\left(f_i - \frac{\frac{a_i g_i}{\sigma^2} + \frac{\mu(f_{i-})}{\tau^2}}{\frac{a^2}{\sigma^2} + \frac{1}{\tau^2}}\right)^2\right\}$$

In the above lemma, it is noted that $E(f_i|g_i)$ can be seen to be a weighted average of the data and prior mean where the weights are based on the choice of $\sigma$ and $\tau$. Under this situation, samples are iteratively drawn from the posterior distribution using Gibbs sampling. The Gibbs sampling procedure ensures convergence to the MAP estimate of the true image after a sufficient number of iterations.

One issue in the proposed MRF-MAP formulation described above is determining an appropriate value of $\alpha$. A prerequisite for determining an appropriate value of $\sigma$ is to acquire some a priori knowledge on the shape of the mandible within the selected pixel blocks in each CT slice. The inner and outer contours of the portion of the mandible within each of the pixel blocks can be essentially approximated by quadratic polynomials with different coefficients. A quadratic polynomial has the general form:

$$y = c_1 x^2 + c_2 x + c_3 \qquad \text{(Eq. 74)}$$

For estimating the coefficients $c_1$, $c_2$ and $c_3$ in equation (74), three simultaneous equations need to be solved, which means that a set of three points $[(x_1,y_1)(x_2,y_2)(x_3,y_3)]$ on the inner contour and outer contour of the portion of the mandible in each of the pixel blocks in each image slice in the CT image stack is to be obtained. The need to obtain so many data points (six data points per pixel block per CT image slice) can be justified as follows: (1) The inner and outer contours of the mandible, appearing in a particular CT image slice, cannot be represented mathematically by a single quadratic polynomial with appropriate translation parameters along the x and y axes. This is because the curvatures of the inner contour and outer contour of the mandible are observed to be quite different. (2) Since the spatial resolution of the image stack is coarser along the z axis (axial direction) compared to the x and y axes, an inner or outer contour of the mandible in two different slices cannot be mathematically approximated by a single quadratic polynomial. This is due to difference in curvatures of an inner or outer contour in two consecutive CT image slices.

In one embodiment, user interaction (e.g., via computer mouse clicks on the screen) with the system generates all the required data points. Note that a typical set of three points can be located anywhere along the inner or outer contour of the portion of the mandible within the chosen pixel block. Thus, the coefficients of the fitted quadratic polynomial are not particularly sensitive to the choice of the clicked points to the extent that these points lie on the contour (inner or outer) whose equation is being estimated. In some embodiments, the generation of these input data points can be automated in similar manner to that described above. Once the quadratic polynomial for a contour is determined, a set of points satisfying the polynomial (e.g., a set of points along the fitted contour) is generated. Typically, most of the points within the set have high intensity values, since they correspond to bone pixels, whereas only a few have low intensity values since they correspond to pixels at a potential fracture site. For potential fracture pixels at a site i, on a given contour the value of $\alpha$ can be assigned as follows:

$$\alpha_i = g_i \Big/ \max_i(g_i) \qquad \text{(Eq. 75)}$$

where $\max_i(g_i)$ represents the maximum of all the observed pixel intensity values along the contour under consideration.

As to performance, experimental results of the MRF-MAP scheme of the above described embodiments, were observed based on CT images that clearly showed that the two bone fragments involved in the hairline fracture were not visibly out of alignment. This fact helps exploit the bilateral symmetry between the two halves of the mandible, despite the presence of the hairline fracture. Whereas the original intensity values at the fracture pixel sites were low (due to bone loss), the reconstructed (restored) intensity values at these sites were high, (which correspond to the bone pixel intensities) on account of MAP estimation via repetitive Gibbs sampling. Illustration of the observed images can be found in the provisional application by which the current disclosure obtain priority, and hence is incorporated by reference in its entirety.

Hence, the hairline detection approach described above can be generally summarized as comprising a first and second phase. In the first phase, the hairline fractures are localized within pixel blocks of known size by analyzing all the image slices in the CT image stack by exploiting the (approximate) bilateral symmetry of the human mandible and using the statistical correlation coefficient as a measure of intensity mismatch. In each of the aforementioned pixel blocks, an MRF-MAP based approach is used to achieve hairline fracture detection via implicit image restoration. Since the implicit reconstruction embedded within the proposed MRF-MAP based technique is designed to mimic the natural bone healing process in the absence of any surgical intervention, the proposed scheme has an important prognostic significance as well. In addition to its aforementioned clinical significance, the problem of hairline fracture detection also has certain noteworthy aspects of theoretical interest from the perspective of computer vision and pattern recognition research. This is primarily because of the challenging task of dealing with an image with a spatially localized degradation resulting from a mathematically unknown degradation function. Thus, a degradation matrix is computed from the input data (by fitting quadratic polynomial functions to the inner and outer contours) before applying the Gibbs sampling procedure for the MAP estimation.

In some embodiments, the improvised MRF-MAP paradigm described above can be extended to build a 3D target mandible, in case of hairline fractures. Further, though described above as a deterministic approach, in some embodiments, the degradation matrix may be modeled as a stochastic entity by, for instance, imposing a suitable prior distribution (such as a Beta distribution) on the a values. Additionally, some embodiments may be extended to formulations of prior distributions (such as the Inverse-Gamma distribution) for both τ and σ to conform to the hierarchical Bayesian paradigm. In such an implementation, the posterior distribution may use an alternative sampling scheme such as rejection sampling for drawing samples from the posterior distribution.

Figure 19:
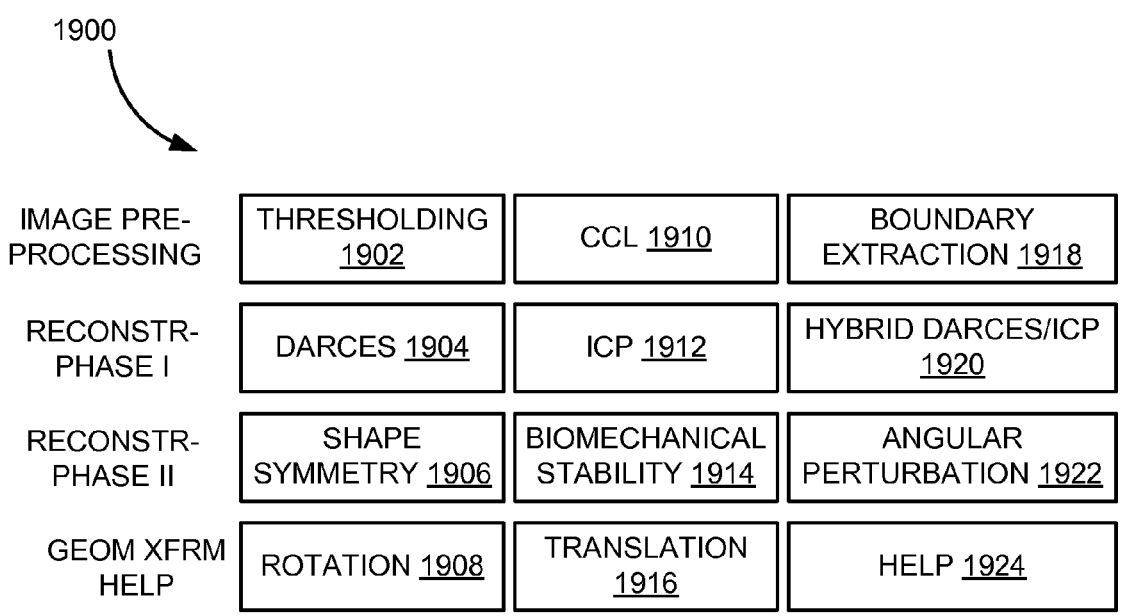
FIG. 19 depicts an embodiment of a graphics user interface by which a user can activate the various operations of the virtual surgical system shown in FIGS. 1 and 2.

FIG. 19 provides an embodiment of a graphics user interface by which a user can activate the various operations of the virtual surgical system shown in FIGS. 1 and 2. For instance, the graphics user interface (GUI) 1900 can be presented to a user to assist the operator is implementing the two-phase approach or other mechanisms also described above. The GUI 1900 comprises an interface to prompt image pre-processing, the first (I) or second (II) reconstruction phases, and geometric transformation (used to finally bring the various bone fragments into registration). Under image pre-processing, button icons include thresholding 1902, CCL 1910, and boundary extraction 1918. Under reconstruction, phase 1, button icons include DARCES 1904, ICP 1912, and hybrid DARCE/ICP 1920. Under reconstruction, phase 11, button icons include shape symmetry 1906, biomechanical stability 1914, and angular perturbation 1922. Under geometric transformation and help, rotation 1908, translation 1916, and help 1924. These various button icons have functionality corresponding to the various methods and operations described above. One having ordinary skill in the art should understand that different GUI configurations, using one or more screen displays, may be used in some embodiments.

It should be emphasized that the above-described embodiments, particularly, any "preferred" embodiments, are merely possible examples of implementations, merely set forth for a clear understanding of the principles of the virtual surgical system. Many variations and modifications may be made to the above-described embodiment(s) without departing substantially from the spirit and principles of the disclosure.

At least the following is claimed:

1. A system for virtually reconstructing a fractured bone, comprising:
   a memory with software stored therein; and
   a processor configured with the software to:
      match fracture surfaces of an imaged fractured bone with a data aligned rigidity constrained exhaustive search (DARCES) surface matching algorithm that uses fracture surface data sets to produce a transformed sample data set for at least one of the fracture surfaces;
      match the fracture surfaces with an iterative closest point (ICP) algorithm that uses the transformed sample data set; and
      minimize a mean-squared error between the matched fracture surfaces based on iterative angular perturbations until a desired reconstruction of the fractured bone is achieved; and
   wherein the processor is further configured with the software to:
      receive image slices corresponding to the imaged bone having a hairline fracture, the image slices each comprising a plurality of pixel blocks;
      fit quadratic polynomial functions to inner and outer contours of the imaged bone for select pixel blocks less than the entire plurality of the pixel blocks for each of the images slices;
      iteratively sample the select pixel blocks based on Markov random field modeling and maximum a posteriori estimation to visualize the hairline fracture; and
      reconstruct the bone at the hairline fracture site in a manner to mimic the natural bone healing process in the absence of any surgical intervention.

2. The system of claim 1, wherein the processor is further configured with the software to:
   receive data corresponding to image slices of the imaged bone comprising a fracture;
   determine potential fracture points of the imaged bone from the data based on a curvature scale space algorithm;
   filter out one or more of the potential fracture points; and
   determine which of the remaining fracture points are stable across a predetermined number of the image slices based on a Kalman filter that provides surface data for the fracture.

3. The system of claim 1, wherein the processor is further configured with the software to:
   identify at least two fracture surface pairs based on a maximum weight graph matching algorithm;
   model the fracture surfaces as vertices of a general graph;
   compile a score matrix comprising edge weights between the vertices of the fracture surface pairs to determine opposing fracture surface pairs; and
   register the opposing fracture surface pairs.

* * * * *